(12) United States Patent
Minakuchi et al.

(10) Patent No.: US 8,233,750 B2
(45) Date of Patent: Jul. 31, 2012

(54) IMAGE MANAGEMENT SYSTEM, REPORT CREATION TERMINAL, MEDICAL IMAGE MANAGEMENT SERVER, AND IMAGE MANAGEMENT METHOD

(75) Inventors: Maki Minakuchi, Otawara (JP); Kenichi Niwa, Otawara (JP); Akira Goto, Otawara (JP); Ichirou Maeda, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 883 days.

(21) Appl. No.: 12/062,209

(22) Filed: Apr. 3, 2008

(65) Prior Publication Data

US 2008/0247676 A1 Oct. 9, 2008

(30) Foreign Application Priority Data

Apr. 6, 2007 (JP) ................. 2007-100155

(51) Int. Cl.
*G06K 9/54* (2006.01)
*G06K 9/00* (2006.01)
(52) U.S. Cl. ........................ 382/305; 382/128
(58) Field of Classification Search .............. 382/305, 382/100, 128–134; 705/2
See application file for complete search history.

(56) References Cited

U.S. PATENT DOCUMENTS

| | | | |
|---|---|---|---|
| 6,912,531 B1 | 6/2005 | Matsumoto et al. | |
| 7,289,651 B2 * | 10/2007 | Vining et al. | 382/128 |
| 7,492,970 B2 * | 2/2009 | Saito et al. | 382/305 |
| 7,680,308 B2 * | 3/2010 | Dale | 382/128 |
| 2004/0107118 A1 * | 6/2004 | Harnsberger et al. | 705/2 |
| 2005/0219664 A1 | 10/2005 | Niwa | |
| 2005/0226405 A1 | 10/2005 | Fukatsu et al. | |
| 2006/0271403 A1 | 11/2006 | Iwasa et al. | |
| 2008/0212855 A1 * | 9/2008 | Shibuya et al. | 382/128 |

FOREIGN PATENT DOCUMENTS

| | | |
|---|---|---|
| JP | 2001-043239 | 2/2001 |
| JP | 2001-167213 | 6/2001 |
| JP | 2003-038447 | 2/2003 |
| JP | 2005-301453 | 10/2005 |
| JP | 2005-316990 | 11/2005 |
| JP | 2006-271483 | 10/2006 |
| JP | 2007-087285 | 4/2007 |

OTHER PUBLICATIONS

Office Action issued Feb. 21, 2012 in Japanese Application No. 2007-100155 filed Apr. 6, 2007.

* cited by examiner

*Primary Examiner* — Yon Couso
(74) *Attorney, Agent, or Firm* — Oblon, Spivak, McClelland, Maier & Neustadt, L.L.P.

(57) ABSTRACT

Enhanced image data is stored, and medical image data contained in the enhanced image data and a screen for creating an interpretation report are displayed on a monitor. In response to a linking operation, link data containing image specification information specifying medical image data to link in the enhanced image data is generated and included into data of the interpretation report. In response to an operation of requesting linked medical image, based on the link data, medical image data indicated by the image specification information within the enhanced image data is specified from the enhanced image data, and the specified medical image data is outputted to a requesting destination of the linked medical image. Thus, a link can be set to medical image data that is one data element within enhanced image data, and only a linked data row can be extracted and read from the enhanced image data.

16 Claims, 27 Drawing Sheets

FIG. 7

| StackID:2<br>TindexID:3 | MEMORY ADDRESS NUMBER | OFFSET VALUE |
|---|---|---|
| StackID:2<br>TindexID:3 | 301ᵀᴴ TO 400ᵀᴴ | 30Kbyte |
| ... | ... | |
| StackID:2<br>TindexID:4 | 601ᵀᴴ TO 700ᵀᴴ | 900Kbyte |
| ... | ... | |

FIG. 8

| | | SPECIFICATION INFORMATION OF ENHANCED IMAGE DATA 100 | | | EXISTING LOCATION INFORMATION |
|---|---|---|---|---|---|
| | IP ADDRESS OF IMAGE MANAGEMENT SERVER | TYPE OF IMAGE DIAGNOSIS APPARATUS USED FOR IMAGING | PATIENT ID | EXAMINATION ID | |
| http:// | | | | | OFFSET=900 |

FIG. 10

| | SPECIFICATION INFORMATION OF ENHANCED IMAGE DATA 100 | | | IMAGE SEQUENCE INFORMATION 132 |
|---|---|---|---|---|
| IP ADDRESS OF IMAGE MANAGEMENT SERVER | TYPE OF IMAGE DIAGNOSIS APPARATUS USED FOR IMAGING | PATIENT ID | EXAMINATION ID | |
| http:// | | | | StackID=2&TindexID=4 |

FIG. 15

| REPORT READING TERMINAL | NUMBER-OF-SHEET INFORMATION |
|---|---|
| TERMINAL A | 1 |
| TERMINAL B | 0 |
| . . . | |

FIG. 23

| | SPECIFICATION INFORMATION OF ENHANCED IMAGE DATA 100 | | | EXISTING LOCATION INFORMATION | GENERATION INFORMATION |
|---|---|---|---|---|---|
| IP ADDRESS OF IMAGE MANAGEMENT SERVER | TYPE OF IMAGE DIAGNOSIS APPARATUS USED FOR IMAGING | PATIENT ID | EXAMINATION ID | | |
| http:// | | | | OFFSET=900 | 20050101 |

FIG. 24

| RECORD OF ENHANCED IMAGE DATA 100 ||
|---|---|
| GENERATION INFORMATION | CHANGE CONTENT |
| 20040101 | DATA ROW 200K ~ 300K DELETION |
| 20060101 | DATA ROW 500K ~ 600K DELETION |
| 20060601 | DATA ROW 1200K ~ 1300K DELETION |
| 20070101 | DATA ROW 400K ~ 500K DELETION |

FIG. 26

| IP ADDRESS OF IMAGE MANAGEMENT SERVER | SPECIFICATION INFORMATION OF ENHANCED IMAGE DATA 100 | | | IMAGE SEQUENCE INFORMATION 132 | GENERATION INFORMATION |
|---|---|---|---|---|---|
| | TYPE OF IMAGE DIAGNOSIS APPARATUS USED FOR IMAGING | PATIENT ID | EXAMINATION ID | | |
| http:// | | | | StackID=2&TindexID=4 | 20060101 |

FIG. 27

| RECORD OF ENHANCED IMAGE DATA 100 ||
|---|---|
| GENERATION INFORMATION | CHANGE CONTENT |
| 20070101 | StackID:2, Tindex:4 → StackID:2, Tindex:3 |
| | StackID:2, Tindex:5 → StackID:2, Tindex:4 |
| | . . . |

IMAGE MANAGEMENT SYSTEM, REPORT CREATION TERMINAL, MEDICAL IMAGE MANAGEMENT SERVER, AND IMAGE MANAGEMENT METHOD

BACKGROUND OF THE INVENTION

1. Field of the Invention

The present invention relates to a technology of setting a link to medical image data contained in enhanced image data composed of a plurality of medical image data recorded in one file, and extracting the medical image data contained in the enhanced image data, based on the link.

2. Description of the Related Art

A medical image diagnosis apparatus captures an image of a subject and creates medical image data. A medical image diagnosis apparatus is, for example, an X-ray CT apparatus, an MRI apparatus, an ultrasound diagnosis apparatus, and a nuclear medical diagnosis apparatus. Medical image data generated by a medical image diagnosis apparatus is managed by a server for managing an image, and is readable at a terminal within a network. A report creation terminal for assisting creation of an interpretation report receives medical image data from the server, and displays on a monitor. This report creation terminal is used for interpretation of a medical image. An interpretation report is a document describing a problem presumed form interpretation of a displayed medical image by an interpreting doctor.

For example, as disclosed in Japanese Unexamined Patent Application Publication JP-A 2005-301453, there is a case in which the report creation terminal links medical image data to an interpretation report. The report creation terminal generates link data indicating the storage destination of medical image data, and embeds the link data into an interpretation report. To embed into an interpretation report means a process of including the link data into data of the interpretation report. In a conventional technology, each medical image data composes one file, so that it is possible to include the name of a file into link data and thereby specify medical image data to link.

In recent years, in the DICOM standard, a concept of enhanced image data (also referred to as bundle image data or multi-frame image data) composed of a plurality of medical image data recorded in one file, has appeared. In this DICOM standard, a plurality of medical image data generated by a medical image diagnosis apparatus are compiled in one file. In a case in which each medical image data composes one file, there is a need for establishment of communication every time the medical image data is sent and/or received. Therefore, numerous interactions between an apparatus sending the medical image data and an apparatus receiving the data are required, whereby an enormous load on the communication traffic is generated. On the contrary, in the case of the enhanced image data, all medical images can be sent and/or received in one communication, and therefore, numerous interactions are not required. Consequently, the load on the communication traffic is reduced.

However, for reading an interpretation report, it is enough to acquire only a medical image that should be referred to. Medical image data actually cited in an interpretation report is only part of the enhanced image data. However, a conventional linking method is a method in which a file name is included in the link data, and the file name does not exist in the medical image data recorded in the enhanced image data. Therefore, in the case of employing the conventional linking method, it is necessary to receive the entire enhanced image data. As a result, a significant amount of time is required to display desired medical image data, and the efficiency of medical practices using an interpretation report as a reference is extremely decreased. In some terminals reading an interpretation report, resources cannot tolerate such large volume of enhanced image data, and the decrease of the medical efficiency in this case is significant. Moreover, in a case in which the entire enhanced image data is received, an enormous load is generated in the communication traffic within the network.

SUMMARY OF THE INVENTION

An object of the present invention is to provide a technology of setting a link to medical image data contained in enhanced image data composed of a plurality of medical image data recorded in one file, and specifying the medical image data contained in the enhanced image data, based on the link.

An image management system in a first aspect of the present invention comprises: a storage configured to store enhanced image data containing a plurality of medical image data in one file; a first display device configured to display the medical image data contained in the enhanced image data, and display a screen for creating an interpretation report; a generator configured to generate link data containing image specification information specifying medical image data to link within the enhanced image data, in response to a linking operation in the first display device; a link processor configured to include the generated link data into data of the interpretation report; a specification processor configured to specify medical image data indicated by the image specification information within the enhanced image data, from the enhanced image data stored in the storage, based on the link data, in response to an operation of requesting a linked medical image; and an output part configured to output the specified medical image data to a requesting destination of the linked medical image.

A report creation terminal in a second aspect of the present invention is a report creation terminal configured to display a plurality of medical image data contained in enhanced image data and display a report creation screen for an interpretation report, and comprises: a generator configured to generate link data containing image specification information specifying medical image data to link within the enhanced image data, in response to a linking operation; and a link processor configured to include the generated link data into data of an interpretation report.

A medical image management server in a third aspect of the present invention is provided with a storage configured to store enhanced image data containing a plurality of medical image data in one file and is configured to transmit, to a terminal displaying an interpretation report, medical image data linked to the interpretation report, and the medical image management server comprises: a receiver configured to receive link data containing image specification information specifying the linked medical image data within the enhanced image data, from the terminal; a specification processor configured to specify medical image data specified by the image specification information included in the link data, from the enhanced image data; and an output part configured to output the medical image data specified by the specification processor, to the terminal.

An image management method in a fourth aspect of the present invention comprises: storing enhanced image data containing a plurality of medical image data in one file, into a storage; displaying the medical image data contained in the enhanced image data, and a screen for creating an interpretation report, on a monitor; in response to a linking operation using an input device, generating link data containing image specification information specifying medical image data to link within the enhanced image data, and including the generated link data into data of the interpretation report; in response to an operation of requesting a linked medical image by using an input device, specifying the medical image data indicated by the image specification information within the enhanced data, from the enhanced image data; and the specified medical image data is output to the requesting destination of the linked medical image, based on the link data.

According to the first to fourth aspects of the present invention, it is possible to set a link to medical image data that is one data element within enhanced image data, and extract and read only a linked data row from the enhanced image data. Therefore, the need for linking the entire enhanced image data is eliminated, whereby communication traffic is reduced in reading an interpretation report. Further, an effort for searching medical image data actually cited in an interpretation report from enhanced image data having been transmitted is omitted, whereby the clinical efficiency increases.

In a fifth aspect of the present invention, in a case where the record sequence of medical image data within enhanced image data is changed, or part of the medical image data is deleted from the enhanced image data, it is possible to: store a change history that includes the content of the change and generation information of the enhanced image data accompanying the change; further include the generation information into link data at the time of generation of the link data; and when specifying linked medical image data, specify medical image data indicated by image specification information included in the link data, within enhanced image data of a current generation, based on the change history and the generation information contained in the link data.

According to the fifth aspect of the present invention, even if the content of the enhanced image data is changed, it is possible to keep linking appropriate medical image data by using the link data within the interpretation report created before the change, which is extremely effective in linking.

In a sixth aspect of the present invention, it is possible to configure so as to: include image sequence information of medical image data, into enhanced image data; when specifying a linked medical image, specify the specific number of sheets preceding and following in the sequence of images of the specified medical image data, in addition to medical image data specified by image specification information; and output a specified medical image to a requesting destination.

According to the sixth aspect of the present invention, it is not necessary to separately acquire medical images preceding and following the medical image cited in an interpretation report, or link the preceding and following images at the time of creation of an interpretation report, whereby the clinical efficiency and the interpretation efficiency increase.

The image specification information may be existing location information that indicates the existing location within enhanced image data of medical image data to link, and medical image data existing in the location indicated by the existing location information may be specified from the enhanced image data. The existing location information may be an offset value from the beginning of the enhanced image data, and the medical image data starting from data indicated by the offset value may be specified.

The image specification information may be image sequence information of medical image data to link, and medical image data corresponding to the image sequence information may be specified from enhanced image data. Further, the image sequence information may contain a pair of group information to which each medical image data belongs and in-group sequence information indicating the sequence of images within the group, and medical image data corresponding to the group information and the in-group sequence information may be specified from the enhanced image data. The group information and the in-group sequence information are, for example, a Stack ID and Tindex ID provided in DICOM, respectively, or a Tindex ID and a Stack ID provided in the DICOM, respectively.

BRIEF DESCRIPTION OF THE DRAWINGS

FIG. 7 shows an example of a file structure management table created when enhanced image data is expanded.

FIG. 8 shows link data with existing location information.

FIG. 10 shows link data with image sequence information.

FIG. 15 shows a table for setting the number of transmitted sheets.

FIG. 23 is an example showing data configuration of link data created so as to contain existing location information and generation information.

FIG. 24 is an example showing a change history recorded in an image database.

FIG. 26 shows data configuration of link data created so as to contain image sequence information and generation information.

FIG. 27 is another example showing a change history recorded in an image database.

DETAILED DESCRIPTION OF THE EMBODIMENT

Figure 1:
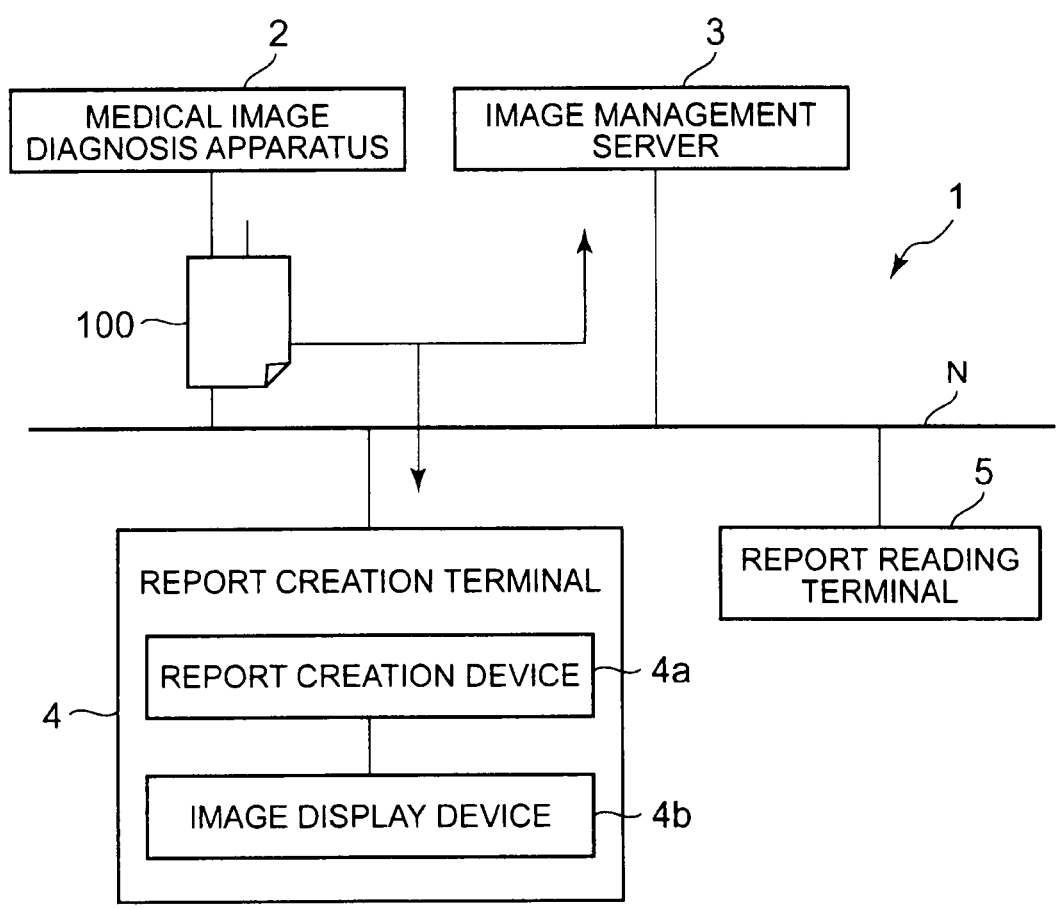
FIG. 1 shows a system configuration of a medical image management system.

Hereinafter, an embodiment of a technology according to the present invention of setting a link to medical image data contained in enhanced image data and specifying the medical image data within the enhanced image data based on the link will be described in detail referring to the drawings.

(Configuration of Medical Image Management System)

FIG. 1 is a view showing a system configuration of a medical image management system according to an embodiment of a link-setting technology.

A medical image management system 1 is a system that stores medical image data received from a medical image diagnosis apparatus 2 so as to be available for reading. The medical image diagnosis apparatus 2 is a so-called modality such as an X-ray CT apparatus, an MRI apparatus, an ultrasound diagnosis apparatus and a nuclear medical diagnosis apparatus. The medical image diagnosis apparatus 2 captures an image of a subject, and transmits medical image data, which is the result of the capture, to the medical image management system 1. The medical image data is data showing an image of the inside of the subject's body.

The medical image management system 1 is configured by connecting an image management server 3, a report creation terminal 4 and a report reading terminal 5 via a network N. The image management server 3, the report creation terminal 4 and the report reading terminal 5 are each composed of a so-called computer, and each has at least a CPU, an HDD, a RAM and a communication interface. The report creation terminal 4 and the report reading terminal 5 are composed by connecting an input device such as a keyboard and a mouse, and a monitor such as a CRT display and a liquid crystal display, to the computer. The image management server 3, the report creation terminal 4 and the report reading terminal 5 are each equipped with an operating system and a control application that operates on the operating system. The operating system and the control application are read out from the HDD and expanded to the RAM when triggered by input/output of data or by an operation by an operator, and then the CPU commands execution. With this execution, the data is inputted and/or outputted via the communication interface. There is a case in which a plurality of medical image diagnosis apparatuses 2, report creation terminals 4 and report reading terminals 5 are installed on the network N. As for the report reading terminal 5, there is a case in which each of the plurality of units has individual performance and a difference in performance arises.

In the medical image management system 1, when medical image data is generated in the medical image diagnosis apparatus 2, the medical image diagnosis apparatus 2 transmits the medical image data to the image management server 3. The image management server 3 registers and then stores the received medical image data into the database. When requested for interpretation of a medical image, an interpreting doctor interprets the medical image by using the report creation terminal 4 to create an interpretation report. The interpretation report is document data in which the result of interpretation of a medical image is stated. The report creation terminal 4 receives medical image data from the image management server 3 and displays on a monitor as a first display device, and also displays a report creation screen on the monitor to create an interpretation report in response to the operation of an input device.

A link of the medical image data may be provided to the interpretation report. For example, when an operator drags displayed medical image data and drops into a character string within an interpretation report by using an input device, the report creation terminal 4 generates link data showing the dragged medical image data, and embeds the link data into the data of the interpretation report in association with the character string where the medical image data has been dropped. "To embed" is to include the link data in the data of the interpretation report.

The report creation terminal 4 may be one computer, or may be a terminal composed of two computers: a report creation device 4a creating an interpretation report, and an image display device 4b displaying medical image data. In a case in which the report creation terminal is composed of the report creation device 4a and the image display device 4b, a monitor for displaying a report creation screen is incorporated into the report creation device 4a, a monitor for displaying medical image data is incorporated into the image display device 4b, and the report creation device 4a and the image display device 4b are communicated and interlocked with each other via a LAN connection or the like. For example, through the LAN connection, mutual data communication is established so that the report creation device 4a and the image display device 4b operate in an interlocked manner. As the interlocked operation, for example, a cursor is made to be movable from the monitor of the report creation device 4a to the monitor of the image display device 4b. Further, the report creation device 4a is caused to take over the dragged state of the dragged medical image data. Moreover, the link data of the medical image data is transmitted to the report creation device 4a from the image display device 4b. In addition, the image display device 4b is caused to receive the medical image data in response to an operation performed by the report creation device 4a for requesting the link data.

A doctor having requested the interpretation, such as a doctor in charge, reads the interpretation report by using the report reading terminal 5. The report reading terminal 5 receives the created interpretation report, and displays the interpretation report on the monitor as a second display device. In a case in which an image link character string or the like of the medical image data is embedded in the interpretation report, when the operator selects the link character string by using an input device, the report reading terminal 5 transmits the link data embedded in the interpretation report to the image management server 3, thereby requesting the medical image data shown by the link data. When receiving the link data from the report reading terminal 5, the image management server 3 analyzes the link data, and transmits the medical image data indicated by the link data to the report reading terminal 5. When receiving the medical image data, the report reading terminal 5 displays the received medical image data on the monitor. Here, the report creation terminal 4 may execute display of an interpretation report on the monitor, selection of a link character string by using an input device, or process of transmission of link data.

Medical image data handled in the medical image management system 1 includes medical image data in which each data composes one file (referred to as normal medical image data, hereinafter), and enhanced image data 100 in which a plurality of medical image data are recorded in one file. The enhanced image data 100 is generated when the medical imaging device 2 captures an image of a subject, and is transmitted to the image management server 3. By using the enhanced image data 100, it becomes possible to transmit all of the generated medical image data, in one transmission, whereby the communication traffic is reduced.

Figure 2:
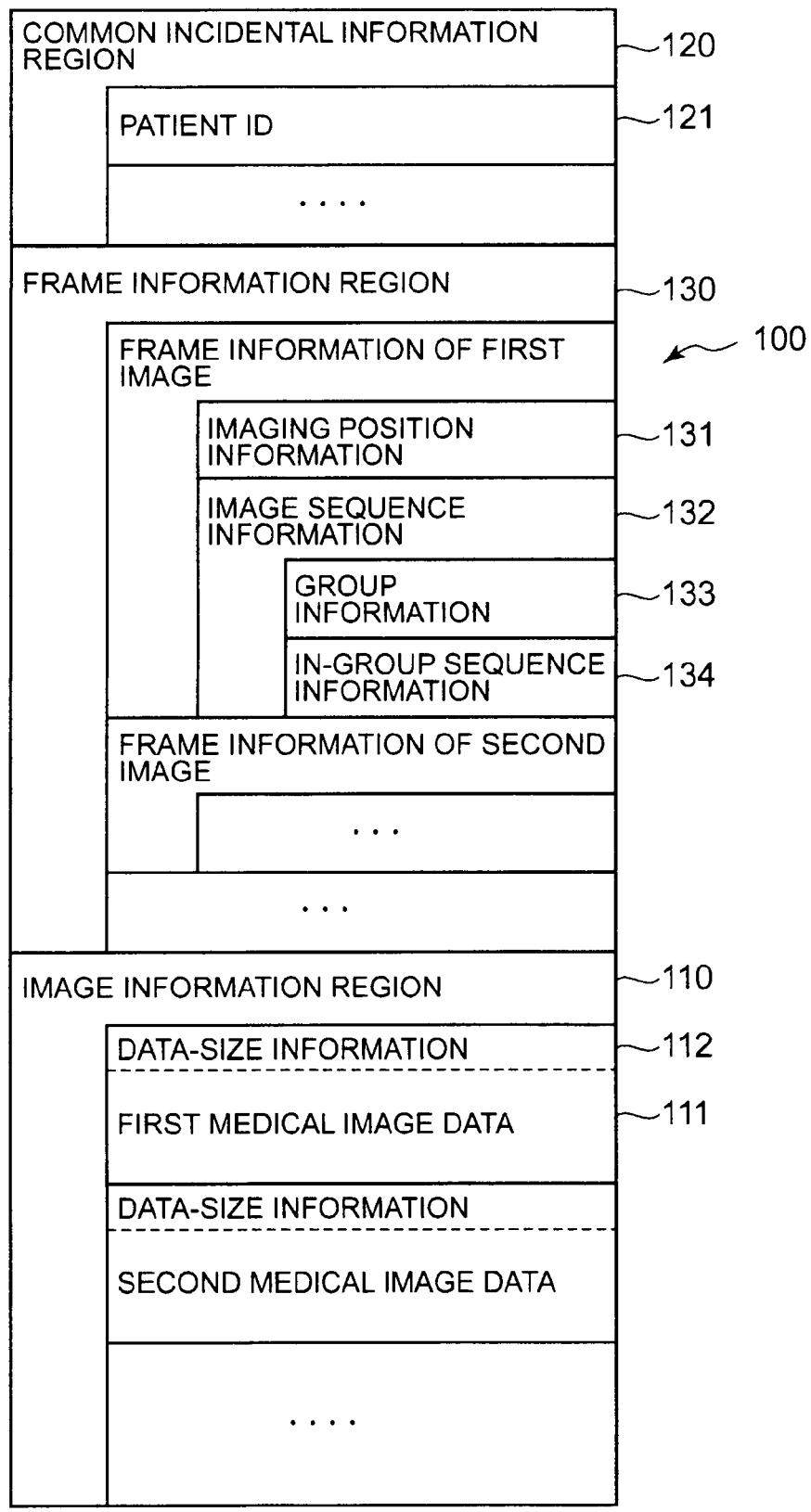
FIG. 2 shows a data configuration of enhanced image data.

FIG. 2 is a view showing a data configuration of the enhanced image data 100 handled by the medical image management system 1. The enhanced image data 100 is composed of three parts: an image information region 110, a common incidental information region 120 and a frame information region 130.

In the image information region 110, medical image data 111 belonging to each series generated in the medical imaging device 2 is recorded. The record sequence of the medical image data 111, namely, the arrangement sequence from the beginning of the data of the medical image data 111 contained in the enhanced image data 100 is random, regardless of a series or a display sequence. For example, a first medical image data 111 may be a third image of a second series, or a second medical image data 111 may be a fifth image of a first series. Here, a "series" represents a group of certain medical image data 111, and the medical image data is divided into series for each imaged site or each imaging condition. It is possible to divide in such a manner that a first series is a group of medical image data acquired by imaging the head part and a second series is a group of medical image data acquired by imaging the abdomen part. It is also possible to divide in such a manner that a first series is a group of medical image data acquired by imaging with administration of a contrast material and a second series is a group of medical image data acquired by imaging without administration of a contrast material.

In the image information region 110, data-size information 112 is added to the beginning of each medical image data 111, and the volume of the medical image data 111 located below the data-size information 112 is described in the data-size information. By adding the data-size information 112, it is possible to recognize on what byte the X-th medical image data 111 exists in the image information region 110.

In the common incidental information region 120, specification information of the enhanced image data 100 is described. For example, the specification information of the enhanced image data 100 includes patient ID 121 of a subject imaged by the medical image diagnosis apparatus 2, examination ID, the type or model name of the medical image diagnosis apparatus 2, series ID or image ID given to the enhanced image data 100 itself, and the like.

In the frame information region 130, individual incidental information of each medical image data 111 recorded in the enhanced image data 100 is described. Specifically, imaging position information 131 and image sequence information 132 are described in the frame information region 130. The imaging position information 131 is information representing the imaging position of the medical image data 111 on the subject by a coordinate system. The image sequence information 132 is information determined by the medical image diagnosis apparatus 2 and added to the medical image data 111, and is also used as information indicating the display sequence when each medical image data 111 contained in the enhanced image data 100 is displayed.

The image sequence information 132 is composed of group information 133 and in-group sequence information 134. The group information 133 indicates a group to which each medical image data 111 recorded in the enhanced image data 100 belongs. The in-group sequence information 134 indicates the sequence number of the medical image data 111 within the group. The group information 133 is given for each series, for example. The in-group sequence information 134 is given for each sequence number within the series, for example. To the enhanced image data 100, a Stack ID is given as the group information 133. To the enhanced image data 100, a Tindex ID (Temporary Index ID) is given as the in-group sequence information 134. For example, in a case in which certain image sequence information 132 shows "SatckID:2" and "TindexID:3," it represents that the medical image data 111 corresponding to this image sequence information 132 is the third medical image data 111 of the second group and, when the enhanced image data 100 is displayed, it is displayed as the third medical image of the second group. The image sequence information 132 may include, other than the Stack ID and the Tindex ID, information provided in DICOM such as Image Type, InStack Position Number, frame acquisition Number and Diffusion sequence. Some medical image diagnosis apparatuses 2 create the enhanced image data 100 so as to associate Tindex ID with the series and associate a Stack ID with the sequence number within the series. The Image Type is information that indicates the type of an image, and the definitions of the TindeX and the Stack ID may be exchanged, depending on the Image Type. In a case in which the image management server 3 manages the enhanced image data 100, and in a case where in which the report creation terminal 4 deconstructs the enhanced image data 100 into the medical image data 111 to display each of them, the definitions of the Stack ID and the Tindex ID are analyzed referring to the Image Type, whereby it is determined which ID shows a series and which ID shows the sequence number within the series.

A pair of the imaging position information 131 and the image sequence information 132 is recorded in the frame information region 130 for each medical image data 111. Further, the pair of the imaging position information 131 and the image sequence information 132 is arranged in a sequence following the record sequence of the medical image data 111 in the image information region 110. Therefore, for the third medical image data 111 of the image information region 110, the series or the sequence number of the medical image data 111 is determined referring to the third image sequence information of the frame information region 130.

Figure 3:
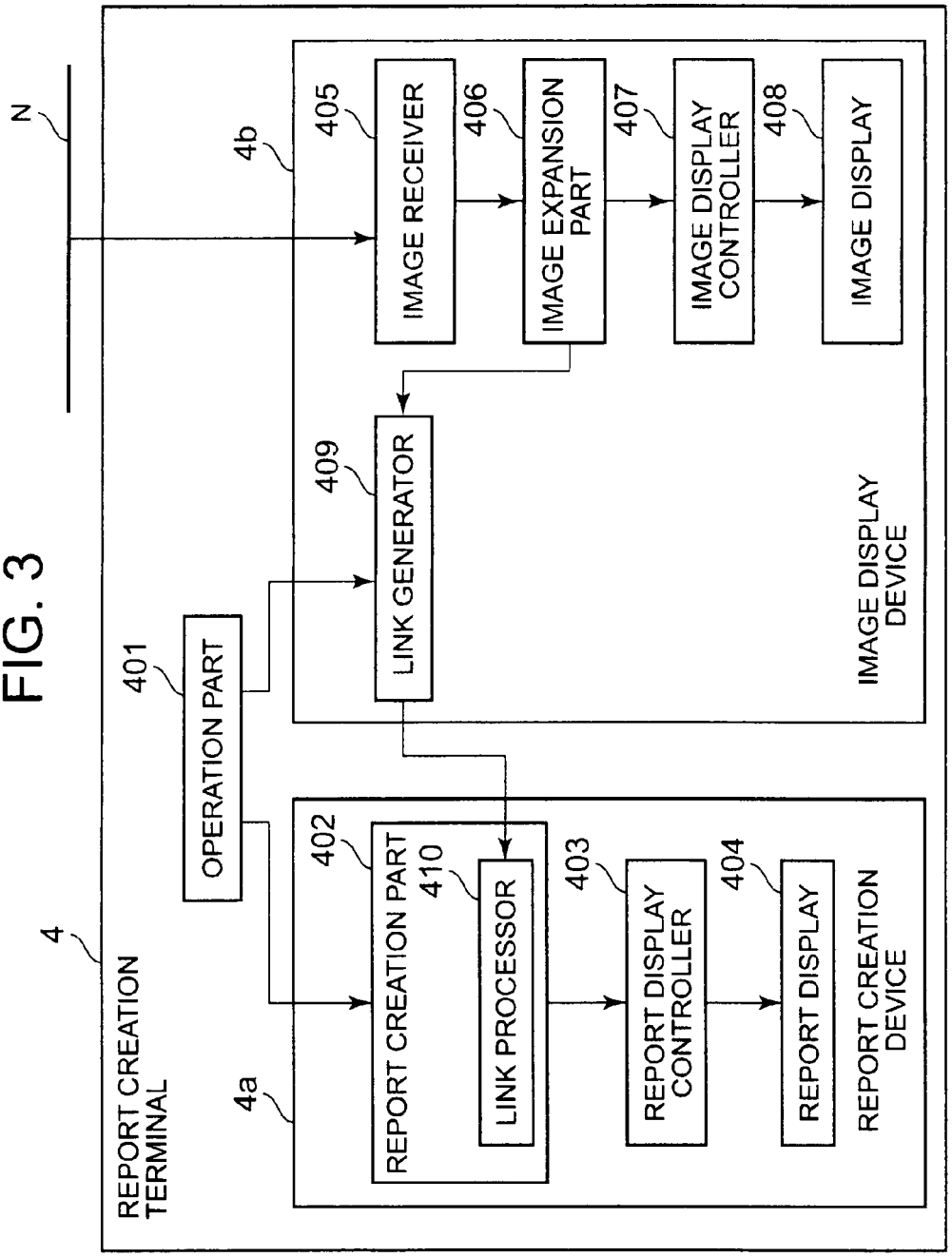
FIG. 3 shows a detailed configuration handling enhanced image data in a report creation terminal.

FIG. 3 is a view showing a detailed configuration handling the enhanced image data 100 in the report creation terminal 4 operated by an interpreting doctor. The report creation terminal 4 executes display of the medical image data 111 to be interpreted, display of a report creation screen, assistance in creation of interpretation reports, and process of linking the displayed medical image data 111 to a character string within an interpretation report.

The report creation terminal 4 comprises an operation part 401. The operation part 401 is composed of an input device operated mainly by an interpreting doctor. The operation part 401 inputs signals indicating a report creation operation and a linking operation to the report creation device 4a and the image display device 4b.

Further, the report creation terminal 4 comprises a report creation part 402, a report display controller 403 and a report display 404, for assisting display of a report creation screen and creation of an interpretation report. Each of these components is implemented by execution of an operating system or a control application by the report creation device 4a of a computer. Each of these components is implemented specifically by a report creation program. The report creation part 402 includes mainly the CPU incorporated into the report creation device 4a. The report creation part 402 creates an interpretation report. In accordance with a press signal inputted from the operation part 401, characters such as letters and symbols associated with the press signal having been inputted are embedded into an interpretation report. The report display controller 403 includes mainly a CPU or GPU incorporated into the report creation device 4a. The report display controller 403 generates drawing data representing a report creation screen and causes the report display 404 to display the drawing data. The report display 404 includes mainly a monitor. The report display controller 403 reflects an interpretation report being created by the report creation part 402 into the drawing data. The interpretation report updated by the report creation part 402 is reflected to the drawing data created by the report display controller 403 in real-time, and is displayed on the report display 404.

Further, the report creation terminal 4 comprises an image receiver 405, an image expansion part 406, an image display controller 407 and an image display 408, for displaying the medical image data 111 to be interpreted. Each of these components is implemented by execution of an operating system or a control application by the image display device 4b of a computer. Each of these components is implemented specifically by a viewer program. The image receiver 405 mainly includes a communication interface. The image receiver 405 receives the normal image data or the enhanced image data 100 from the image management server 3. The image expansion part 406 mainly includes a CPU. The image expansion part 406 deconstructs the enhanced image data into the medical image data 111 included in the enhanced image data 100, and analyzes the enhanced image data 100 to create a file structure management table. The file structure management table is a group of a memory address indicating an expansion destination of the expanded medical image data 111, the image sequence information 132 of the medical image data 111, and the existing location information within the enhanced image data 100. The existing location information is information indicating the location in the enhanced image data 100 where the linked medical image data 111 exists. The existing location information is an offset value indicating on what byte the enhanced image data 100 exists from the beginning. The image display controller 407 mainly includes a CPU or a GPU. The image display controller 407 causes the image display 408 to display each medical image data 111 deconstructed in the image expansion part 406. The image display 408 is a monitor provided in the image display device 4b. The image display controller 407 refers to the file structure management table to display the medical image data 111 in a display sequence according to the in-group sequence information 134, for each group of the medical image data 111. For example, a display region in the monitor is set for each group, and the medical image data 111 of the same group are displayed in the display region so as to be superimposed in accordance with the arrangement sequence. Because the definitions of the "Stack ID" and "Tindex ID" differ depending on the enhanced image data 100, the image expansion part 406 acquires information for identifying the medical image diagnosis apparatus 2 used for imaging, or the Image Type, from the common incidental information region 120 of the enhanced image data 100. Then, the image data is expanded after it is determined which of the group information 133 and the in-group sequence information 134 the Stack ID and the Tindex ID correspond to, by referring to a table showing which of the Stack ID and the Tindex ID represent a group and a sequence, for each of the medical image diagnosis apparatuses 2.

Moreover, the report creation terminal 4 includes a link generator 409 and a link processor 410, for process of linking the displayed medical image data 111 to a character string within an interpretation report. The link generator 409 is provided in the image display device 4b. The link processor 410 is provided in the report creation device 4a. Each of these components is implemented by execution of an operating system (OS) or a control application by the report creation device 4a and the image display device 4b, both of which are computers. Each component of this image display device 4b and the report creation device 4a is implemented specifically by a control program for linking stored in accordance with each role.

The link generator 409 mainly includes a CPU. The link generator 409 generates link data of the medical image data 111 embedded in an interpretation report. When one or a plurality of medical image data 111 displayed on the monitor of the image display device 4b are dragged and dropped into a character string in the interpretation report, the link generator 409 generates each link data for specifying the medical image data 111 having been dragged and dropped. If the medical image data 111 is derived from the enhanced image data 100, the link generator 409 generates image specification information indicating the dragged and dropped medical image data 111 is equivalent to which of the plurality of medical image data 111 recorded in the enhanced image data 100, and includes the same in the link data. The image specification information indicating which of the medical image data 111 among the enhanced image data 100 is linked is either existing location information or image sequence information 132. If an existing data row is specified as the medical image data 111 from a location corresponding to the existing location information, and read from the enhanced image data 100, it is assumed that the linked medical image data 111 is extracted. Further, by counting the arrangement sequence within the frame information region 130 of the image sequence information 132 included in the link data, specifying, from the image information region 110, a data row recorded in the same number of record sequence as the arrangement sequence, as medical image data 111, and is read in from the enhanced image data 100, it is assumed that the linked medical image data 111 has been extracted. "To extract" means to specify the medical image data 111 and the specified medical image data 111. According to the file structure management table created in the image expansion part 406, the image sequence information 132 or the existing location information of the medical image data 111 that is being displayed is specified. By referring to the file generator table, the link generator 409 includes the existing location information or the image sequence information 132 of the linking medical image data in the link data for generating link data.

The link processor 410 mainly includes a CPU. The link processor 410 is implemented by a control program for linking on the report creation device 4a side, which is included in a report creation program for realizing the report creation part 402. The link processor 410 receives, from the image display device 4b side, the link data generated in the link generator 409, and the received link data is linked to a character string subject to dropping and is dropped into an interpretation report. In other words, the link data is included in the data of the interpretation report while being linked to the character string data. Further, when the link is established by the link processor 410, the report display controller 403 causes the report display 404 to display, so as to be able to visually recognize that linking has been done. For example, the report display controller 403 changes the display color of the character string, which was subject to linking, to a blue color or the like, and drawing data with an underlined character string is created and displayed on the report display 404.

Figure 4:
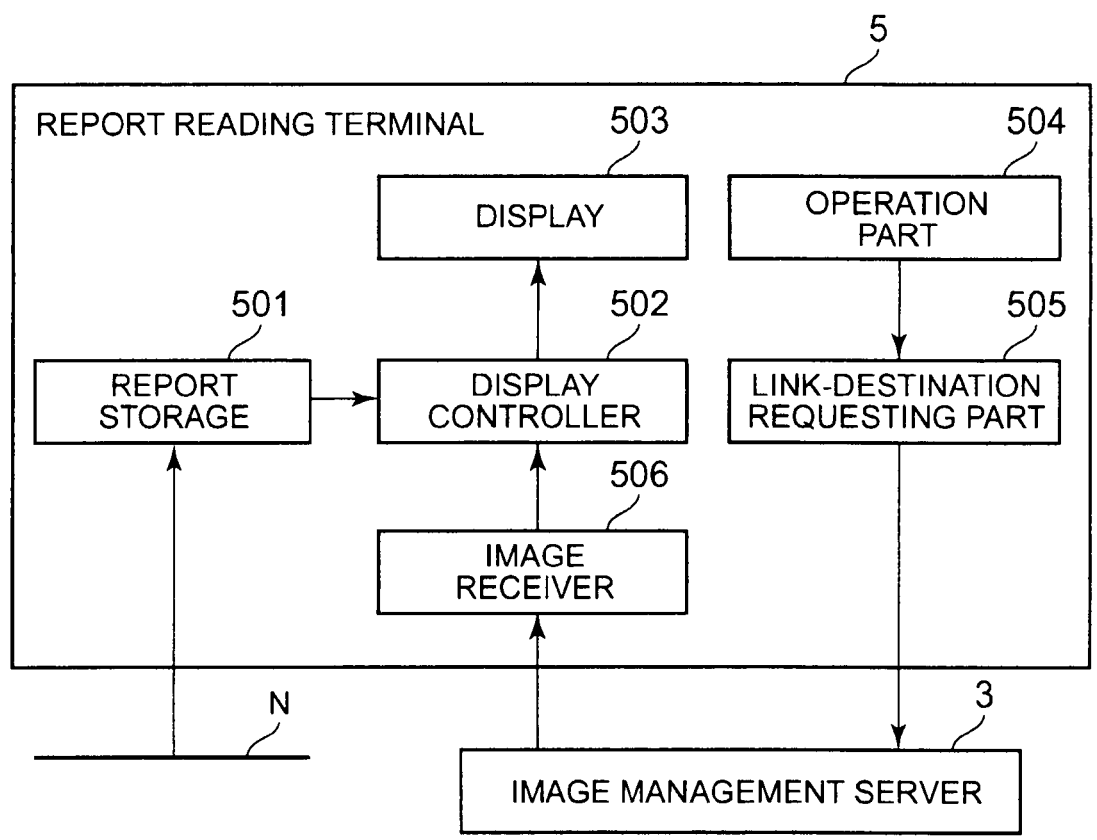
FIG. 4 shows a detailed configuration of a report reading terminal.

FIG. 4 shows a detailed configuration of the report reading terminal 5 operated by a reader of interpretation reports. The report reading terminal 5 displays an interpretation report and displays medical image data 111 linked to the interpretation report. The report reading terminal 5 includes a report storage 501, a display controller 502, a display 505, an operation part 504, a link-destination requesting part 505, and an image receiver 506.

The operation part 504 is composed of an input device operated mainly by a doctor who is to read interpretation reports. The operation part 504 inputs, into the report reading terminal 5, a signal indicating a display operation or a signal indicating an operation requesting the data of a link destination. The display 503 is mainly composed of a monitor. The display 503 displays interpretation reports or linked medical image data 111. The report storage 501 mainly includes a RAM. The report storage 501 temporarily stores an interpretation report to be displayed. The interpretation reports are stored in a report server on the network N (not illustrated), and are received from the report server. The report storage 501 temporarily stores an interpretation report received from the report server.

The link-destination requesting part 505 mainly includes a CPU and a communication interface. The link-destination requesting part 505 generates a command requesting a link destination linked to an interpretation report, and transmits to the image management server 3. When the reader selects a link on the interpretation report by using the operation part 504, the link data is acquired from the interpretation report stored in the report storage 501. Then, the link-destination requesting part 505 transmits the acquired link data to the image management server 3 in the incidental manner to the requirement command.

The image receiver 506 mainly includes a communication interface. The image receiver 506 receives the medical image data 111 from the image management server 3. The image receiver 506 receives the linked medical image data 111 transmitted by the image management server 3 in accordance with the link data transmitted by the link-destination requesting part 505. The display controller 502 mainly includes a CPU or a GPU. The display controller 502 causes the display 503 to display an interpretation report and the medical image data 111. The display controller 502 reads out an interpretation report from the report storage 501, and causes the display 503 to display the interpretation report having been read out. Further, when the image receiver 506 receives, from the image management server 3, the medical image data 111 linked to the interpretation report, the display controller 502 causes the display 503 to display the received medical image data 111.

Figure 5:
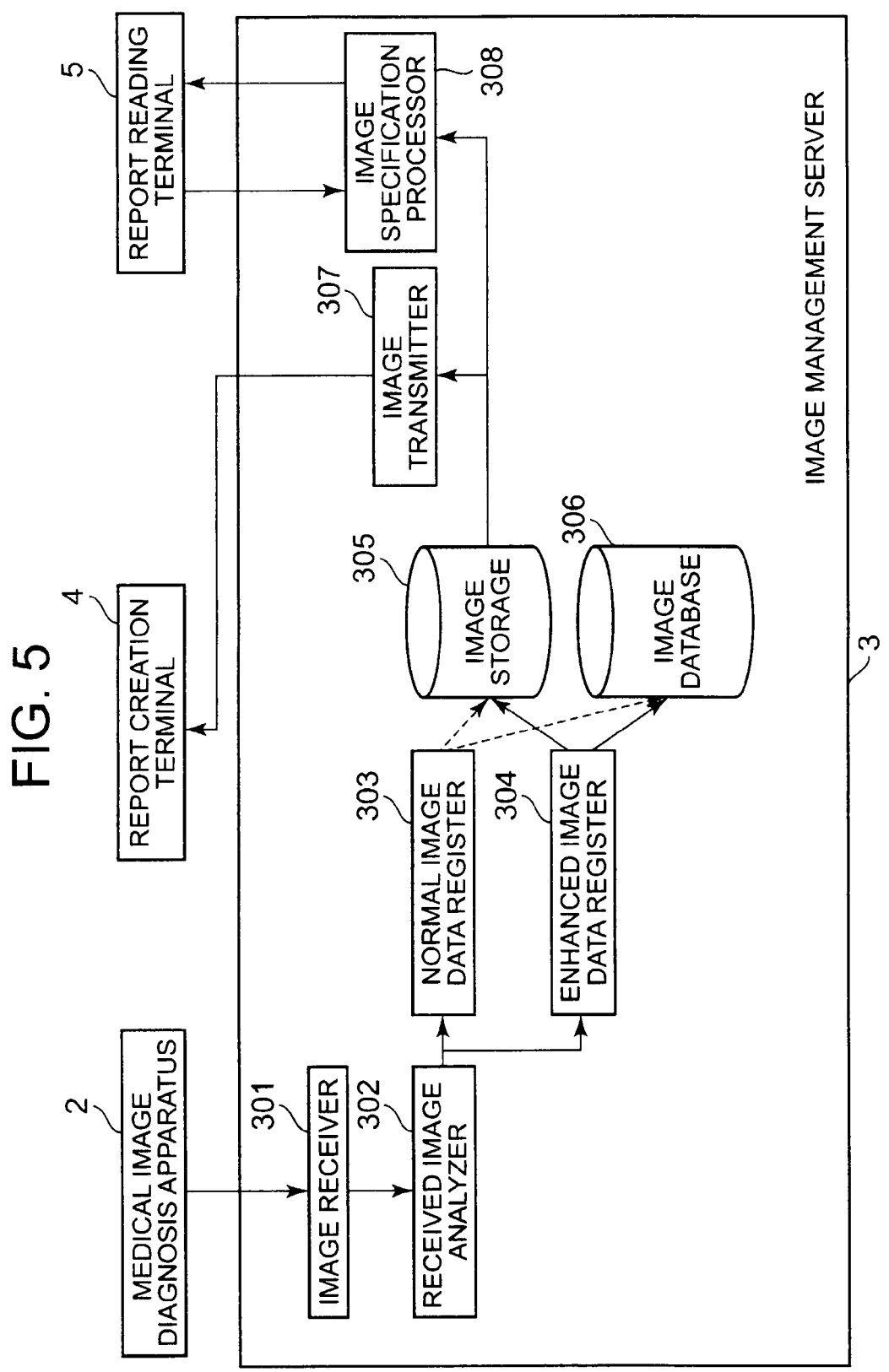
FIG. 5 shows a detailed configuration of an image management server configured to manage enhanced image data.

FIG. 5 is a view showing the detailed configuration of the image management server 3 for managing the enhanced image data 100. The image management server 3 performs management of a database of the normal image data and the enhanced image data 100, transmission of the normal image data and the enhanced image data 100 to the report creation terminal 4, and transmission of the linked medical image data 111.

First, the image management server 3 comprises an image receiver 301, a received image analyzer 302, a normal image data register 303, an enhanced image data register 304, an image storage 305 and an image database 306, for the management of the database of the normal image data and the enhanced image data 100. The respective components are implemented by execution of an operating system or an image management program by the image management server 3 of a computer.

The image receiver 301 mainly comprises a communication interface. The image receiver 301 receives the normal medical image data or the enhanced image data 100 transmitted from the medical image diagnosis apparatus 2. The received image analyzer 302 mainly comprises a CPU. The received image analyzer 302 determines whether the received data is the normal medical image data or the enhanced image data 100. In a case where the frame information region 130 exists as a result of the analysis, the received data is determined to be the enhanced image data 100, and a program for a function as the enhanced image data register 304 is expanded and executed so that the received data is processed in the enhanced image data register 304. In a case where the frame information region 130 does not exist, the received data is determined to be the normal image data, and a program for a function as the normal image data register 303 is expanded and executed so that the received data is processed in the normal image data register 303. In a case where the normal medical image data and the enhanced image data 100 each have information such as a symbol indicating the type thereof, the received image analyzer 302 determines whether it is the normal image data or the enhanced image data with reference to the information. The normal image data register 303 mainly comprises a CPU. The normal image data register 303 registers the received normal image data in the image database 306, and then stores into the image storage 305. The image storage 305 is a so-called storage. The image database 306 mainly comprises an HDD. The image database 306 is a database of the received normal image data or enhanced image data 100. The database stores a record of the image data, which is made by combining the patient name, the patient ID, the type or model name of the medical image diagnosis apparatus 2 used for imaging, and the storage destination indicating the stored location in the image storage 305. The image storage 305 mainly comprises an HDD. The image storage 305 stores the received normal image data or the enhanced image data 100. The normal image data register 303 creates a record of the stored normal image data from the incidental information incidental to the normal image data and from the image storage destination, and then stores into the image database 306. The enhanced image data register 304 mainly comprises a CPU. The enhanced image data register 304 registers the incidental information and image storage destination of the received enhanced image data 100 into the image database 306, and then stores into the image storage 305. When registering the enhanced image data 100 into the image database 306, the enhanced image data register 304, with reference to the common incidental information region 120 and frame information region 130 of the enhanced image data 100, extracts the incidental information of each medical image data 111 recorded in the enhanced image data 100 and a pair of group information 133 and in-group sequence information 134 of each medical image data 111 recorded in the enhanced image data 100, and includes into the record of the enhanced image data 100 for each medical image data 111.

Further, the image management server 3 comprises an image transmitter 307, for the transmission of the normal image data or the enhanced image data 100 to the report creation terminal 4. The respective components are implemented by execution of an operation system or an image management program by the image management server 3 of a computer.

The image transmitter 307 mainly comprises a CPU and a communication interface. The image transmitter 307 transmits the normal image data or the enhanced image data 100 to the report creation terminal 4. When a command requesting a list of image data is transmitted from the report creation terminal 4, the image transmitter 307 searches the image database 306 by using a search key incidental to the command, thereby extracting the corresponding record. When transmitting the extracted record to the report creation terminal 4 and receiving information indicating one image data from the report creation terminal 4, the image transmitter 307 searches the image database 306 to acquire information indicating the storage destination of the image data, and transmits the normal image data or enhanced image data 100 existing within the acquired storage destination to the report creation terminal 4.

Moreover, the image management server 3 comprises an image specification processor 308, for the transmission of the linked medical image data 111. The respective components are implemented by execution of an operating system or an image management program by the image management server 3 of a computer.

The image specification processor 308 mainly comprises a CPU. The image specification processor 308 specifies the linked medical image data 111 from the enhanced image data 100, and transmits to the report reading terminal 5 having requested the link destination. When receiving the link data from the report reading terminal 5, the image specification processor 308 specifies the linked medical image data 111 within the enhanced image data 100 by using image specification information contained in the link data, and reads in the specified medical image data 111. In other words, the image specification processor 308 extracts the linked medical image data 111 from the enhanced image data 100. Then, as an output part, the image specification processor 308 adds the common incidental information region 120 and the frame information region 130 to the extracted medical image data 111, and transmits to the report reading terminal 5. In a case where the image specification information is existing location information, the image specification processor 308 specifies data indicated by the existing location information, and reads in data of the data volume indicated by the data-size information 112 described right after the specified data. The data extracted as a result of the specification and the reading-in is equivalent to the linked medical image data 111. In a case where the image specification information is the image sequence information 132, the image specification processor 308 counts the arrangement sequence in the frame information region 130 of the image sequence information 132, specifies data existing in the same number of record sequence as the arrangement sequence in the image information region 110, as a linked medical image, and reads in data of the data volume indicated in the data-size information 112 from the beginning of the data. The data extracted as a result of the specification and the reading-in is equivalent to the linked medical image data 111. The output includes, other than the transmission to the report reading terminal 5, transmission to the report creation terminal 4 in a case where the report creation terminal 4 comprises the same configuration as the report reading terminal 5 and is a destination requested by the medical image data 111.

Hereinafter, various processes related to the enhanced image data 100 in the medical image management system 1 comprising these components will be described.

(First Mode of Linking Process)

Figure 6:
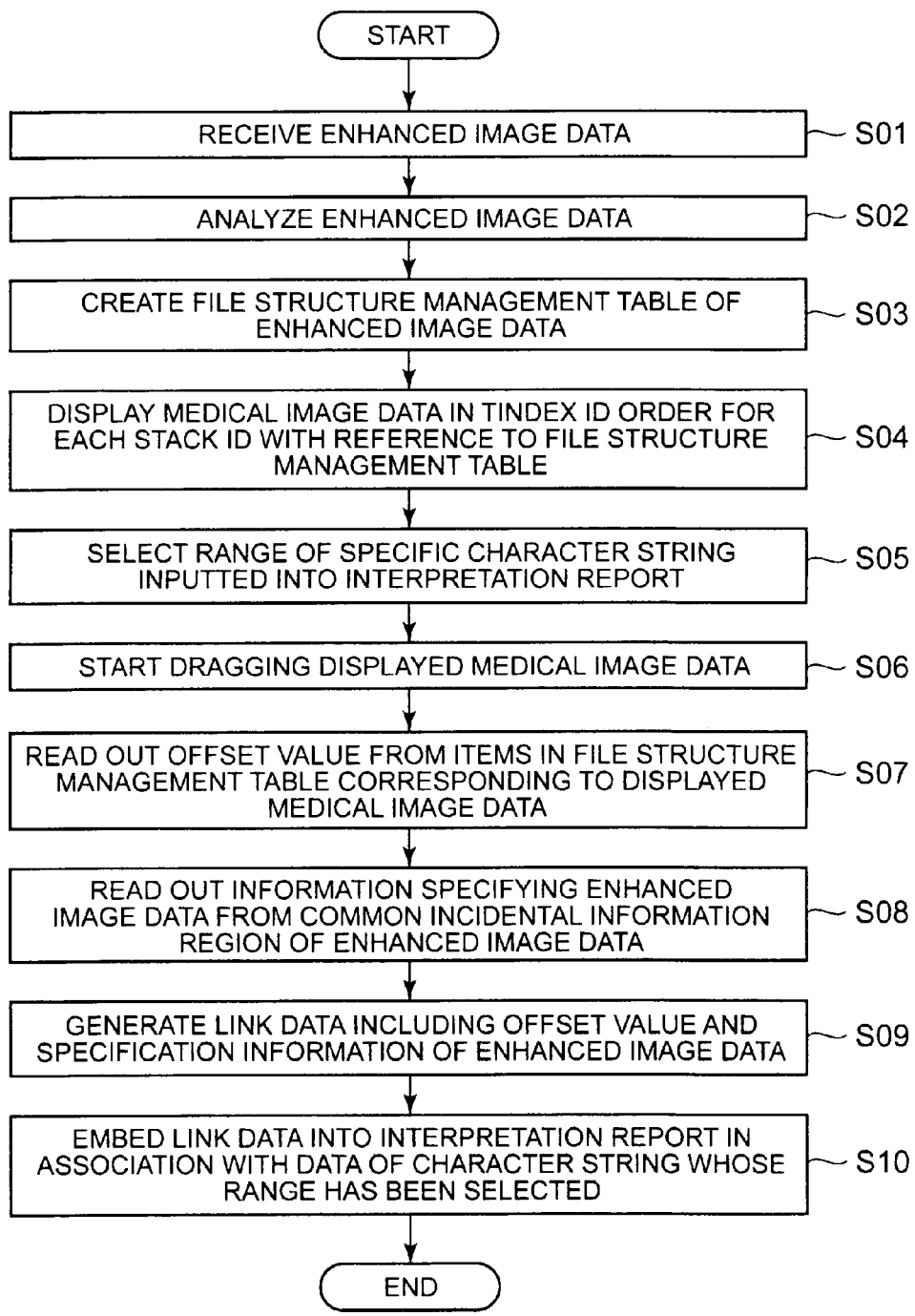
FIG. 6 is a flowchart showing a first mode of a linking operation using existing location information.

First, a linking process in a case where existing location information is included as image specification information into link data will be described. FIG. 6 is a flowchart showing a first mode of a linking operation using the existing location information.

In the report creation terminal 4, when the image receiver 405 receives the enhanced image data 100 from the image management server 3 (S01), the image expansion part 406 analyzes the enhanced image data 100 (S02), and creates a file structure management table of the enhanced image data 100 (S03).

FIG. 7 is a schematic drawing showing an example of a file structure management table created at the time of expansion of the enhanced image data 100. The image expansion part 406 successively deconstructs the enhanced image data 100 into the common incidental information region 120, the frame information region 130 and each medical image data 111, and expands the enhanced image data 100 in the RAM in order from the beginning thereof. At this moment, memory address numbers on the RAM indicating the respective storage regions are stored in the file structure management table. Further, the image expansion part 406 associates with the memory address numbers indicating the storage regions of the common incidental information region 120, the frame information region 130 and each enhance image data 100, and stores a pair of Stack ID and Tindex ID for identifying data stored in the storage regions into the file structure management table. To be specific, at the time of expansion of the medical image data 111 in the RAM, the image sequence information 132 recorded in the same number of arrangement sequence as the expansion sequence in the frame information region 130 is read out as the expansion data identification information as the frame data identification number, and stores into the file structure management table in association with the memory address number of the expanded medical image data 111. Furthermore, when storing the common incidental information region 120, frame information region 130 and each medical image data 111 into the RAM, the image expansion part 406 successively adds the data volumes of the deconstructed data from the data beginning of the enhanced image data 100. The added value is equivalent to the offset value of the following data. The image expansion part 406 stores into the file structure management table in association with this offset value.

After the file structure management table of the enhanced image data 100 is created, the image display controller 407 causes to display the medical image data 111 in the order of Tindex ID for each Stack ID with reference to the file structure management table (S04).

Here, when an operation of displaying the next image is performed by using the operation part 401, the image display controller 407 reads out, from the file structure management table, the memory address number paired with the image sequence information 132 indicating the next sequence of the medical image data 111 currently being displayed, and causes the image display 408 to display the medical image data 111 stored in the storage region in the RAM, which corresponds to the memory address number. For example, as shown in FIG. 7, When an operation of displaying the next image is performed in a state in which the medical image data 111 with Stack ID:2 and Tindex ID:3 is being displayed, the image display controller 407 searches StackID:2 and TindexID:4 from the file structure management table, reads out the medical image data 111 of the storage region corresponding to the address number 601-700 linked to the expansion data identification information in the subject, and causes to display in the image display 408.

When an interpreting doctor uses the operation part 401 to select the range of a specific character string having inputted into an interpretation report (S05) and start dragging the displayed medical image data 111 (S06), the link generator 409 reads out the offset value from the items in the file structure management table corresponding to the displayed medical image data 111 (S07). Furthermore, the link generator 409 reads out information specifying the enhanced image data 100 from the common incidental information region 120 of the enhanced image data 100 (S08).

For example, as shown in FIG. 7, when the medical image data 111 is dragged in a state where the medical image data 111 of Stack ID:2 and Tindex ID:4 is displayed, the offset value of 900 Kbyte is read out from the items related to the medical image data 111 of StackID:2 and TindexID:4 in the file structure management table.

When the offset value and the specification information of the enhanced image data 100 are read out, the link generator 409 generates link data including them (S09).

FIG. 8 is a schematic view showing link data using existing location information. The link generator 409 generates link data made by combining a previously specified IP address of the image management server 3, the specification information of the enhanced image data 100 and the existing location information. The IP address of the image management server 3 is previously stored in the HDD, or inquired from the AE title, etc., of the image management server 3. The specification information of the enhanced image data 100 is, for example, a combination of the type of the medical image diagnosis apparatus 2 used for imaging such as an X-ray CT apparatus and an MRI apparatus, the patient ID of a patient as an information main body of the enhanced image data 100 and the examination ID. The existing location information is an offset value such as 900 Kbyte read out from the file structure management table.

When the link data is generated, the link processor 410 embeds the generated link data into an interpretation report in association with the data of a character string whose range has been selected (S10).

Thus, in the medical image management system 1, it is possible to configure link data as a combination of information specifying the enhanced image data 100 and existing location information indicating the existing location within the enhanced image data 100 of the linked medical image data 111, thereby specifying the enhanced image data 100 and the position therein of the linked data, and setting a link for certain medical image data 111 as one data element within the enhanced image data 100.

In the present embodiment, firstly, the offset value is calculated and the file structure management table is created at the time of image expansion. A storage region for the enhanced image data is secured, the enhanced image data 100 is successively stored from the beginning thereof, and it is determined whether data in a region within the storage region has been dragged. Furthermore, the result of calculation of the position of the storage region of the dragged data in the entire enhanced image data 100 is set as the offset value.

Moreover, it is also possible to write offset-value information in addition to the imaging position information 131 and the image sequence information 132 at the stage of generating the enhanced image data 100 into the frame information of each medical image data 111 stored in the enhanced image data 100, and then include the additionally written offset-value information into the link data as the existing location information.

(Second Mode of Linking Process)

Next, a linking process in the case of including the image sequence information 132 into link data will be described.

Figure 9:
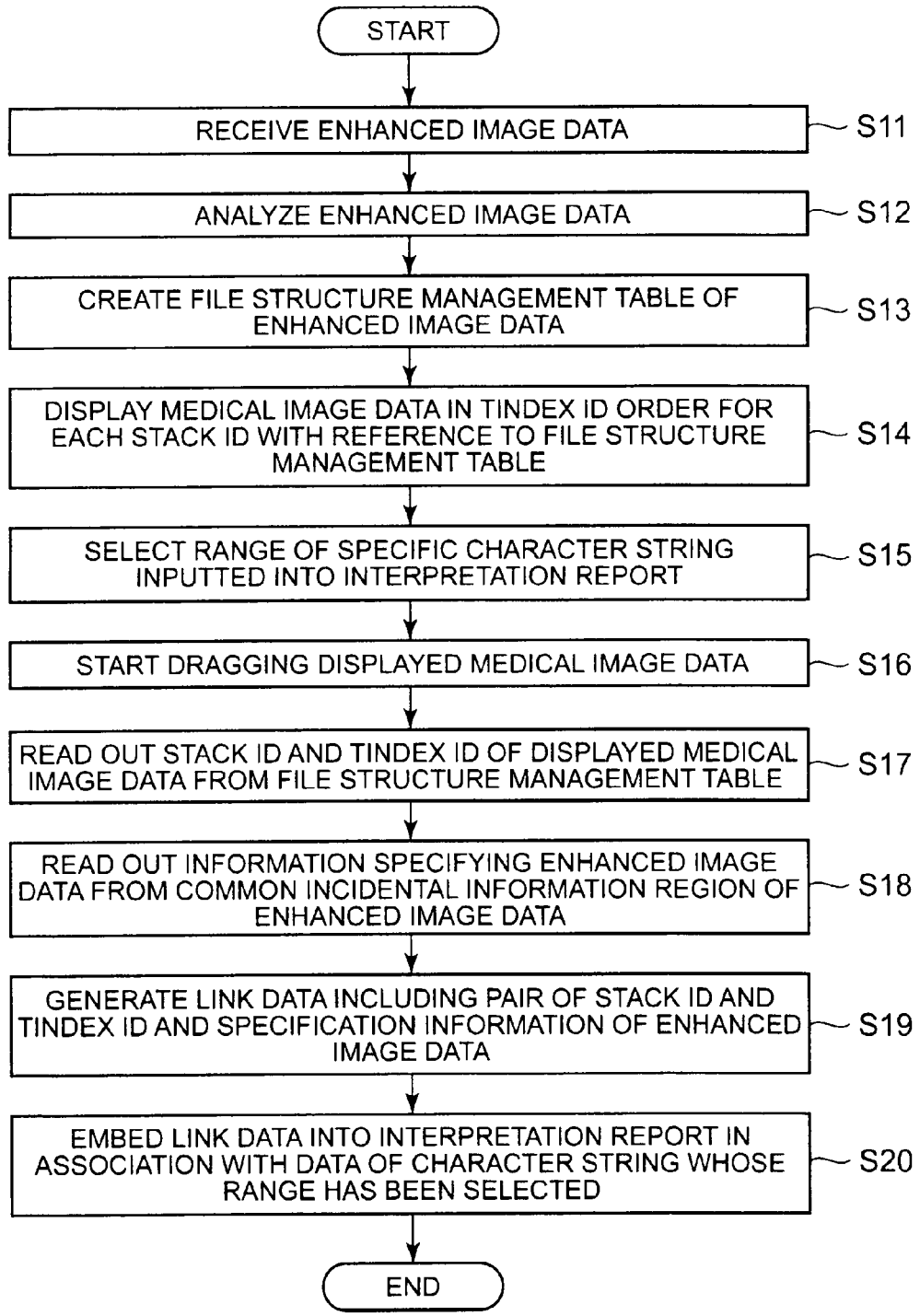
FIG. 9 is a flowchart showing a second mode of a linking operation using image sequence information.

FIG. 9 is a flowchart showing a second mode of the linking operation using the image sequence information 132.

In the report creation terminal 4, when the image receiver 405 receives the enhanced image data 100 from the image management server 3 (S11), the image expansion part 406 analyzes the enhanced image data 100 (S12), and creates a file structure management table (refer to FIG. 7) of the enhanced image data 100 (S13). When the file structure management table of the enhanced image data 100 is created, the image display controller 407 causes to display the medical image data 111 in order of the Tindex ID for each Stack ID with reference to the file structure management table (S14). When the interpreting doctor uses the operation part 401 to select a range of a specific character string inputted in the interpretation report (S15) and start dragging the displayed medical image data 111 (S16), the link generator 409 reads out a Stack ID and a Tindex ID from the items in the file structure management table corresponding to the displayed medical image data 111 (S17). Furthermore, the link generator 409 reads out information specifying the enhanced image data 100 from the common incidental information region 120 of the enhanced image data 100 (S18). For example, as shown in FIG. 7, when the medical image data 111 is dragged in a state in which the medical image data 111 of StackID:2 and TindexID:4 is displayed, the StackID:2 and the TindexID:4 are read out from the items related to the medical image data 111 displayed in the file structure management table. When the StackID and TindexID of the dragged medical image data 111 and the specification information of the enhanced image data 100 are read out, the link generator 409 generates link data including them (S19). FIG. 10 is a schematic view showing link data using the image sequence information 132. The link generator 409 generates link data made by combining the previously specified IP address of the image management server 3, the specification information of the enhanced image data 100, and the image sequence information 132. The image sequence information 132 is, for example, StackID:2 and TindexID:4, which have been read out from the file structure management table. When the link data is created, the link processor 410 embeds the generated link data into an interpretation report in association with the data of the character string whose range has been selected (S20).

(Transmission Process of Linked Image, Corresponding to the First Linking Process)

Figure 11:
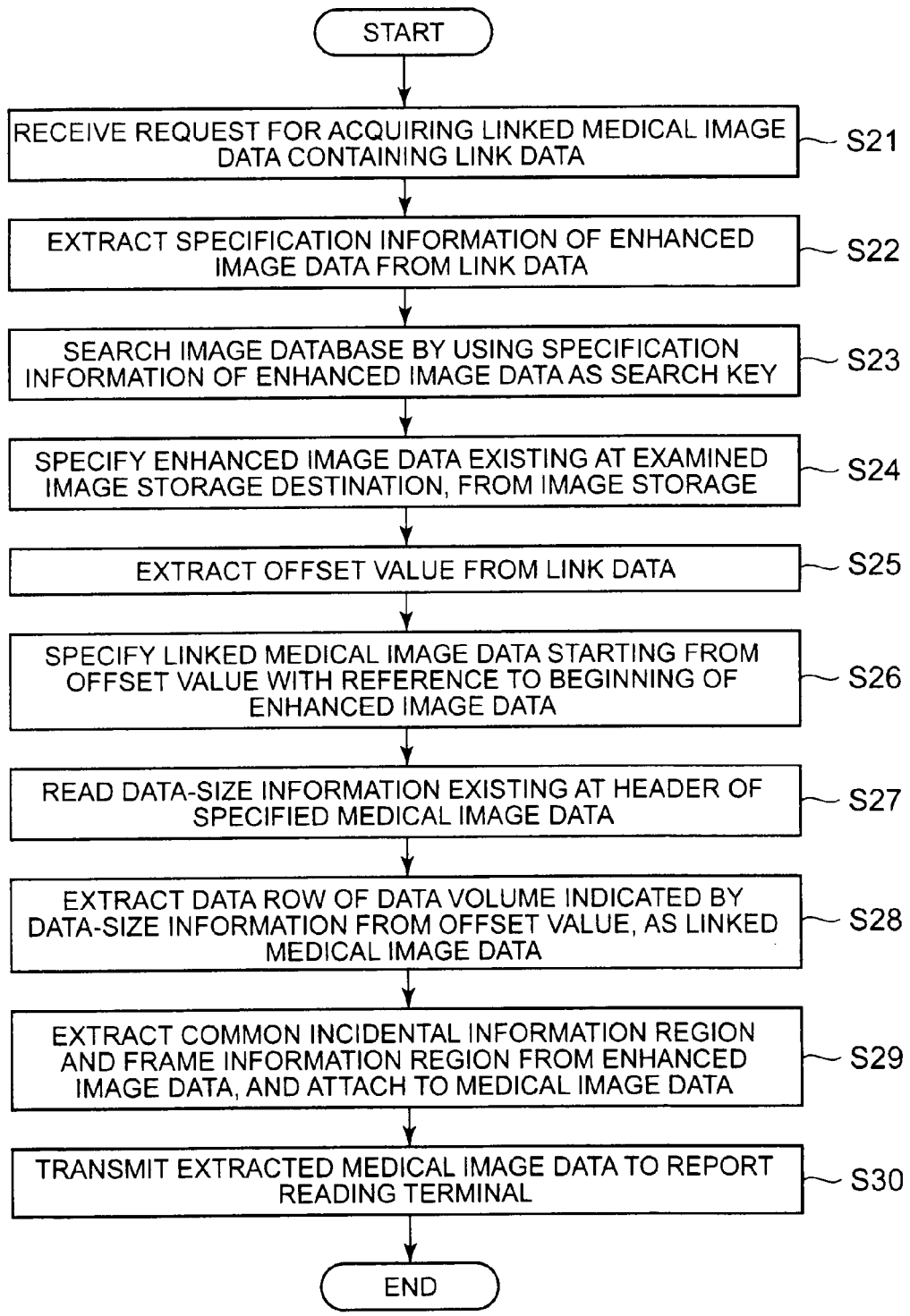
FIG. 11 is a flowchart showing an operation of transmitting linked medical image data, based on link data with existing location information.
Figure 12:
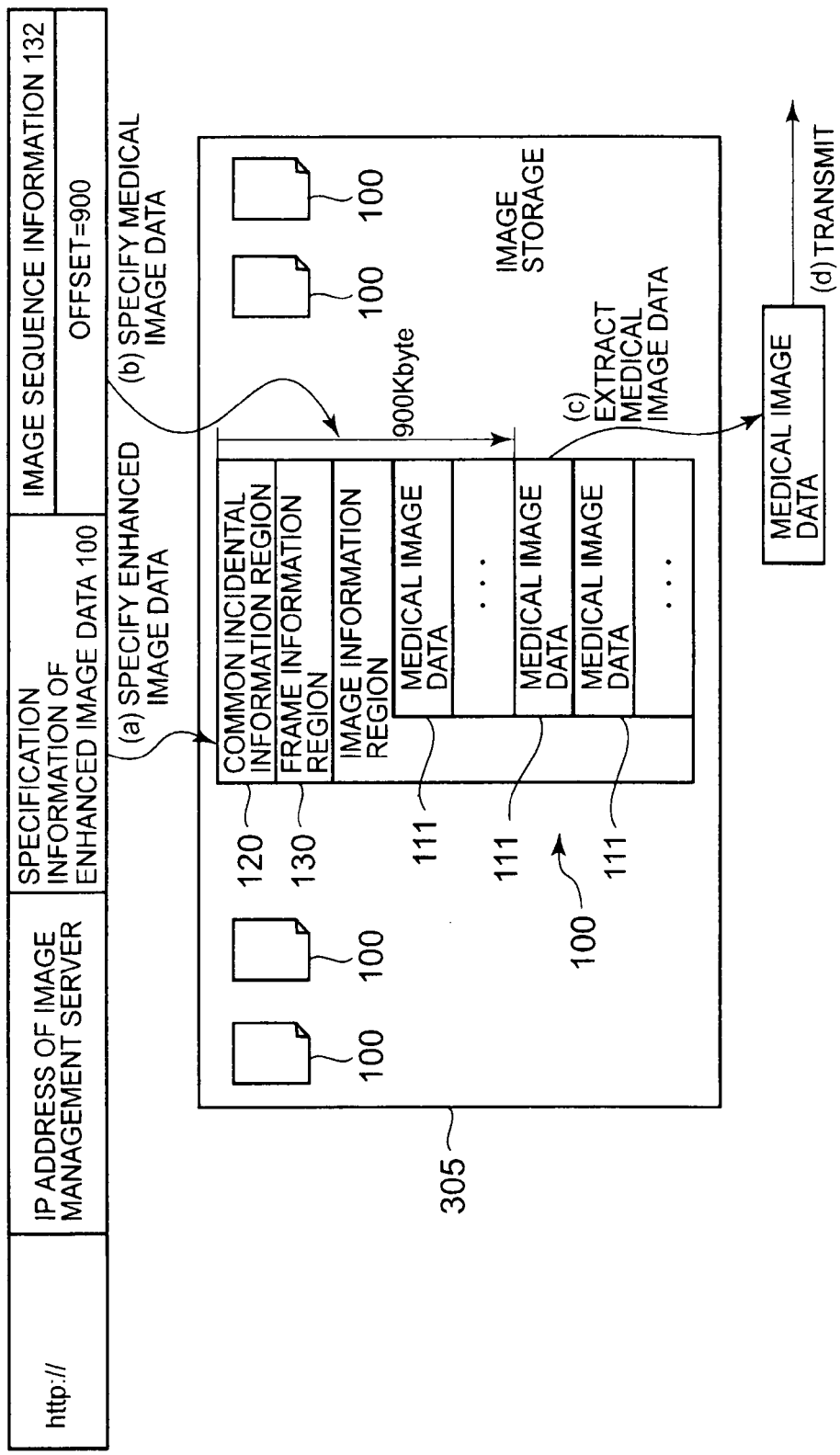
FIG. 12 shows a mode of transmitting medical image data, based on link data with existing location information.

Next, a process for transmitting a medical image of a link destination in a case where existing location information is included in link data as image specification information will be described. FIG. 11 is a flowchart showing an operation of transmitting the linked medical image data 111 to the report reading terminal 5, based on the link data using the existing location information. Further, FIG. 12 is a schematic view showing a mode of transmitting the medical image data 111.

First, when the image management server 3 receives a request for acquiring the linked medical image data 111 containing link data, from the report reading terminal 5 (S21), the image specification processor 308 extracts specification information of the enhanced image data 100 from the link data (S22). When extracting the specification information of the enhanced image data 100, as shown in FIG. 12A, the image specification processor 308 searches the image database 306 by using the specification information as a search key (S23), acquires information indicating the image storage destination paired with the search key, and specifies, from the image storage 305, the enhanced image data 100 existing at the storage destination indicated in the information indicating the image storage destination (S24). Next, as shown in FIG. 12B, the image specification processor 308 extracts an offset value from the link data (S25), and specifies the linked medical image data 111 starting from the offset value with reference to the beginning of the enhanced image data 100 (S26). For example, if the offset value is 900 Kbyte, the medical image data 111 starting from the 900 Kbyte of data from the beginning of the enhanced image data 100 is specified. When the medical image data 111 is specified, as shown in FIG. 12C, the image specification processor 308 reads the data-size information 112 existing at the header of the medical image data 111 (S27), and extracts the data row with the data volume indicated in the data-size information 112 from the offset value, as the linked medical image data 111 (S28). Then, as shown in FIG. 12D, the image specification processor 308 extracts the common incidental information region 120 and a necessary part of the frame information region 130 from the enhanced image data 100 to attach the same to the medical image data 111 (S29) and transmits the extracted medical image data 111 to the report reading terminal 5 (S30).

(Transmission of Linked Image, Corresponding to the Second linking Process)

Figure 13:
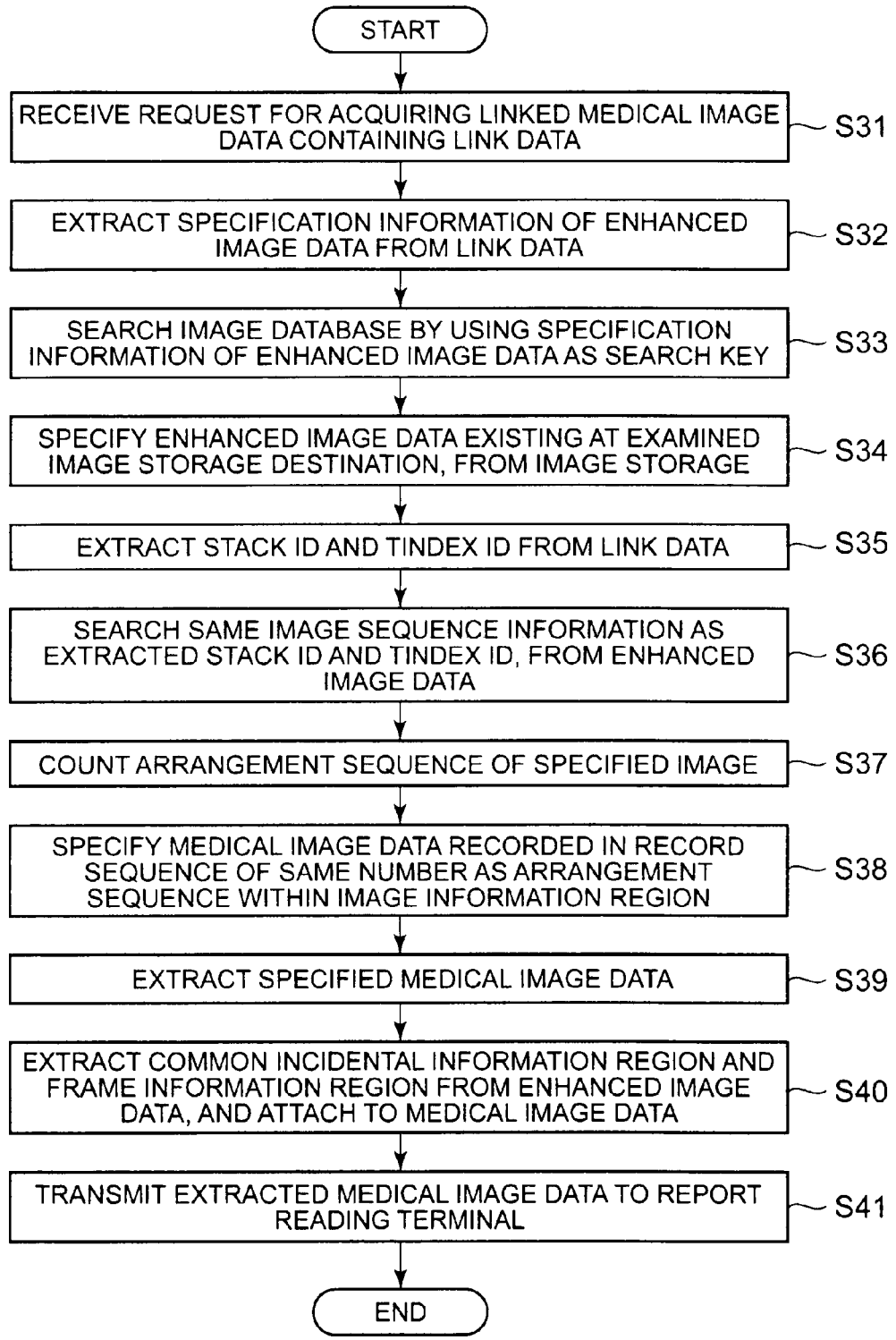
FIG. 13 is a flowchart showing an operation of transmitting linked medical image data, based on link data with image sequence information.
Figure 14:
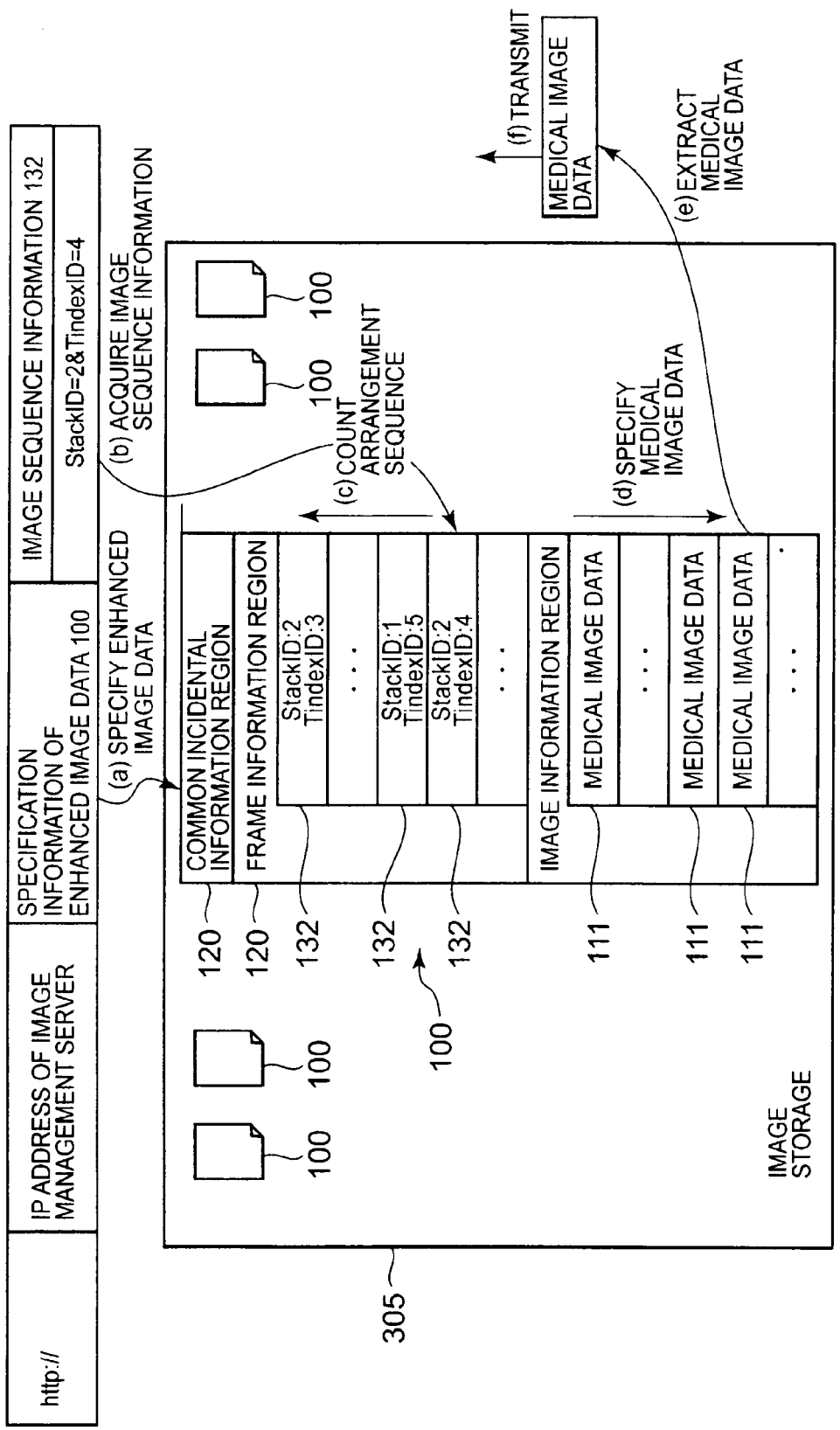
FIG. 14 shows a mode of transmitting medical image data, based on link data with image sequence information.

The transmission of a medical image of a link destination when including image sequence information 132 in link data as image specification information will be described. FIG. 13 is a flowchart showing the operations of transmitting the linked medical image data 111 to the report reading terminal 5, based on the link data using the image sequence information 132. Furthermore, FIG. 14 is a schematic drawing showing the mode of transmitting the medical image data 111.

First, when the image management server 3 receives a request for acquiring linked medical image data 111 containing link data, from the report reading terminal 5 (S31), the image specification processor 308 extracts specification information of the enhanced image data 100 from the link data (S32). When the specification information of the enhanced image data 100 is extracted, as shown in FIG. 14A, the image specification processor 308 searches the image database 306 using the specification information as a search key (S33), acquires information indicating the image storage destination paired with the search key, and specifies, from the image storage 305, enhanced image data 100 existing at the storage destination indicated by the information indicating the image storage destination (S34). Next, as shown in FIG. 14B, the image specification processor 308 extracts a StackID and a TindexID from the link data (S35), and searches, in the frame information region 130 of the enhanced image data 100, image sequence information 132 that is the same as the extracted StackID and the TindexID (S36) from the enhanced image data 100. For example, when the StackID:2 and the TindexID: 4 are extracted from the link data as image sequence information 132, the image sequence information 132 indicating the StackID:2 and the TindexID: 4 is searched from the enhanced image data 100. When the image sequence information within the enhanced image data 100 is specified, as shown in FIG. 14C, the image specification processor 308 counts the arrangement sequence of the specified image sequence information 132 (S37). When the arrangement sequence is specified, the image specification processor 308 specifies medical image data 111 recorded in the same number of record sequence as the arrangement sequence, within the image information region 110, following the data-size information 112 (S38), as shown in FIG. 14D. As shown in FIG. 14E, when medical image data 111 is specified from the enhanced image data 100, the image specification processor 308 extracts the medical image data 111 (S39). Then, as shown in FIG. 14F, the image specification processor 308 extracts the common incidental information region 120 and the frame information region 130 from the enhanced image data 100 to attach the same to the medical image data 111 (S40), and transmits the extracted medical image data 111 to the report reading terminal 5 (S41).

(Modification of the Transmission of Linked Images)

The medical image management system 1 related to the modification additionally transmits a plurality of sheets of medical image data 111 arranged before and after the linked medical image data 111, to the report reading terminal 5. The image specification processor 308 further comprises an HDD and has a number-of-transmitted-sheet setting table. FIG. 15 is a schematic drawing showing the number-of-transmitted-sheet setting table. The number-of-transmitted-sheet setting table stores information on the number of sheets other than the linked medical image data 111 to be transmitted to the report reading terminals 5, in the paired state with information indicating each of a plurality of report reading terminals 5 existing on the network N. In a case where the number-of-sheet information is 1, in addition to the medical image data 111 linked to the report reading terminal 5 with which the number-of-sheet information is associated, medical image data 111 of the preceding one and the following one of the medical image data 111 to which the image sequence has been linked, are also transmitted. If the number-of-sheet information is 0, only the linked medical image data 111 is transmitted.

Figure 16:
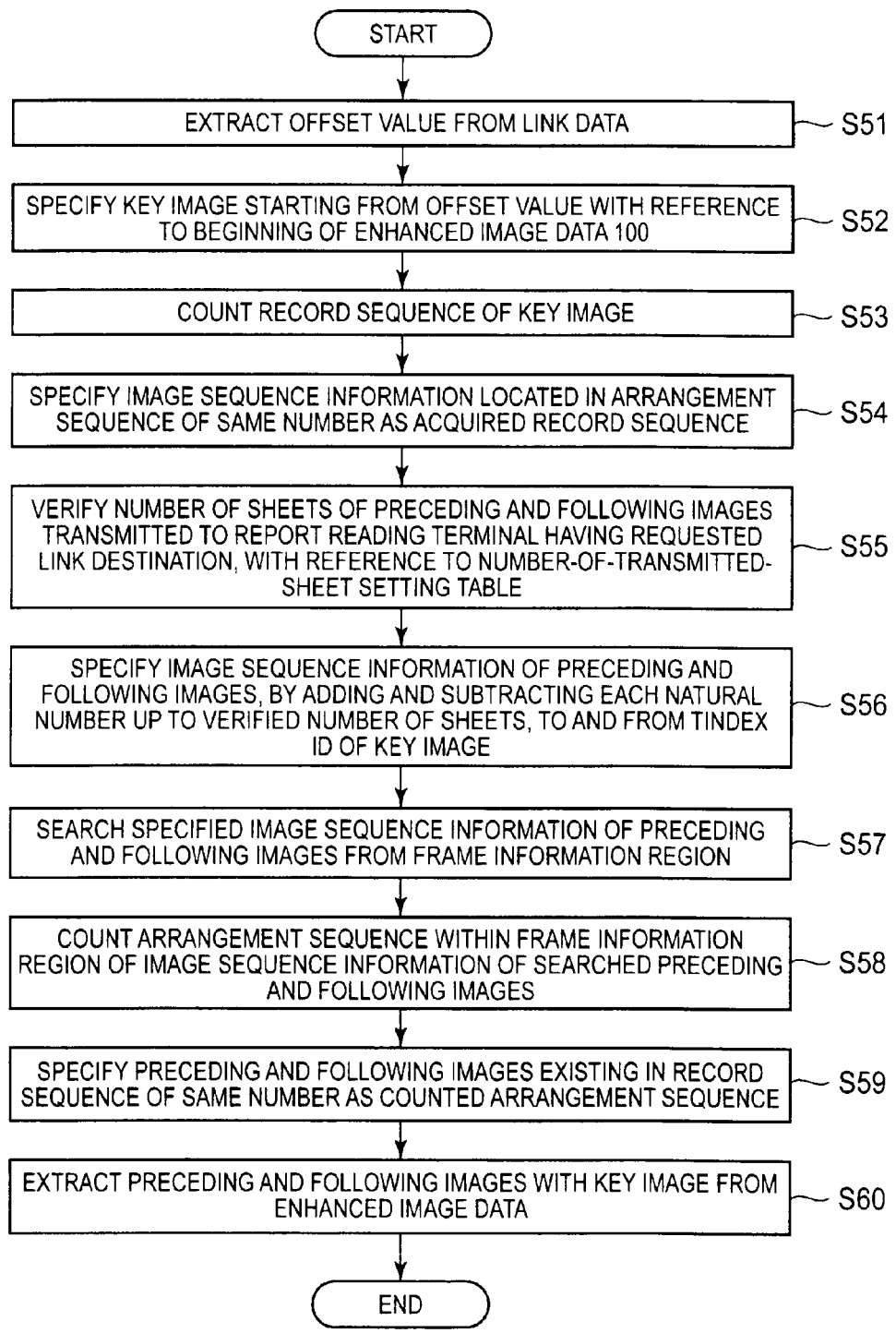
FIG. 16 is a flowchart showing a modification of an operation of transmitting linked medical image data, based on link data containing existing location information.
Figure 17:
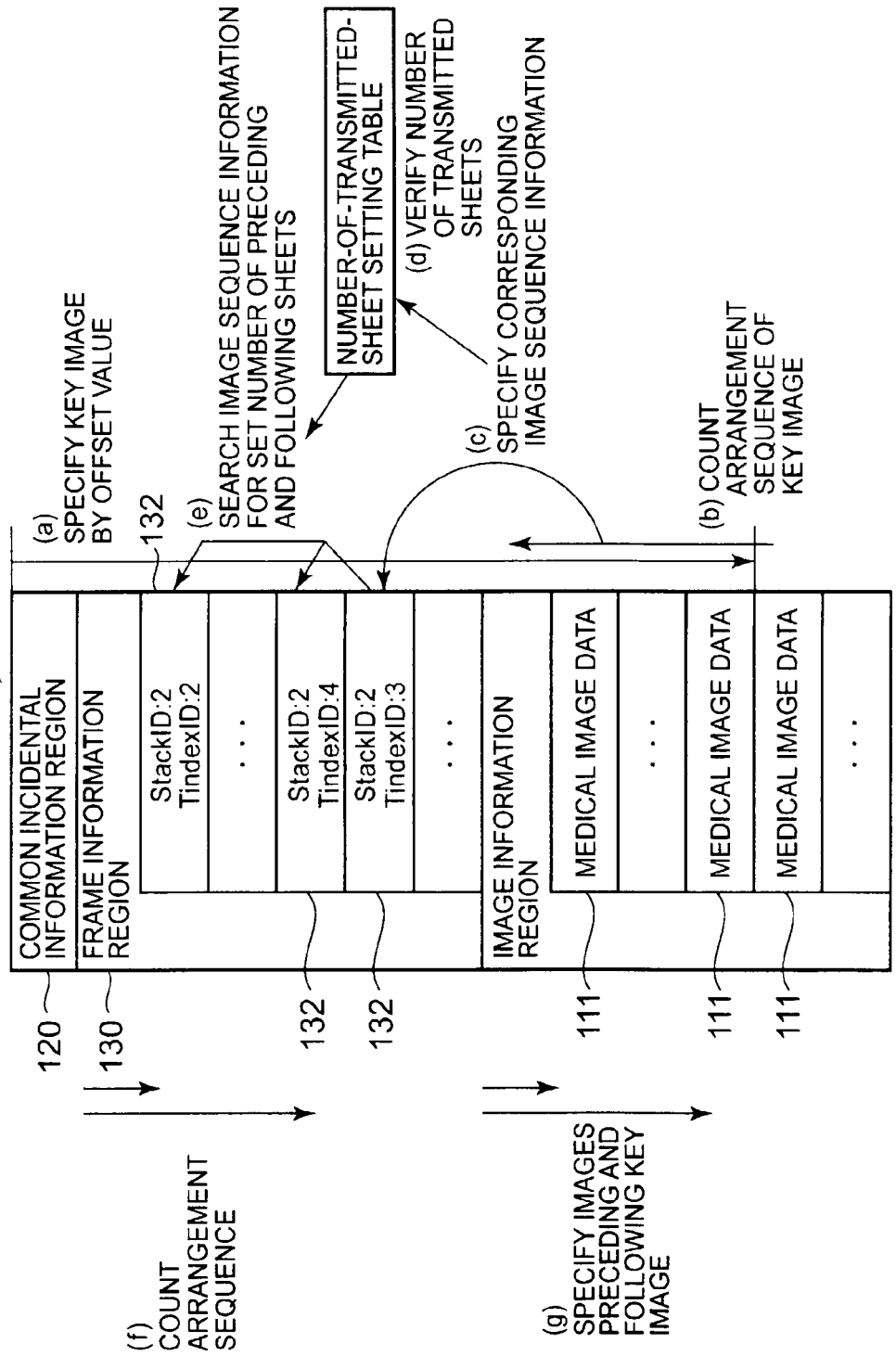
FIG. 17 shows a mode of extracting a plurality of medical images by using link data containing existing location information.

FIG. 16 is a flowchart showing the modification of the operations for transmitting, to the report reading terminal 5, the medical image data 111 that has been linked by link data containing existing location information. Furthermore, FIG. 17 is a schematic drawing showing a mode for extracting a plurality of medical images using link data containing the existing location information.

When the image management server 3 receives link data from the report reading terminal 5 and specifies enhanced image data 100, as shown in FIG. 17A, the image specification processor 308 extracts an offset value from the link data (S51) and specifies linked medical image data 111 starting from the offset value with the reference to the beginning of the enhanced image data 100 (S52). The linked medical image data 111 is called a key image. When the key image is specified, as shown in FIG. 17B, the image specification processor 308 counts the record sequence in the image information region 110 of the medical image data 11 to become the key image (S53), and specifies image sequence information 132 located in the arrangement sequence, which is the same number as the acquired record sequence, in the frame information region 130, as shown in FIG. 17C (S54). As shown in FIG. 17D, the image specification processor 308 verifies each number of sheets of the medical image data before and after the key image other than the key image to be transmitted to the report reading terminal 5, which has requested the link destination with reference to the number-of-transmitted-sheet setting table (S55). The medical image data 111 to be transmitted before and after the key image other than the key image are referred to as preceding and following images. Then, as shown in FIG. 17E, the image specification processor 308 specifies the image sequence information 132 of the preceding and following images, by adding and subtracting each natural number to and from the TindexID of the key image, up to the verified number of sheets (S56), and searches from the frame information region 130 (S57). For example, if the image sequence information 132 of a key image is StackID:2 and TindexID:3, and the number-of-sheet information associated with the report reading terminal 5 having transmitted the link data in the number-of-transmitted-sheet setting table is 1, the image sequence information 132 of the StackID:2 and the TindexID:2 and the image sequence information 132 of the StackID:2 and the TindexID:4 are searched from the frame information region 130. When the image sequence information 132 of the preceding and following images are searched, as shown in FIG. 17F, the image specification processor 308 counts the arrangement sequence of the searched image sequence information 132 of the preceding and following images within the frame information region 130 (S58), and as shown in FIG. 17G, specifies the preceding and following images existing in the record sequence that is the same number as the counted arrangement sequence (S59), and extracts the same from the enhanced image data 100 (S60). Then, the preceding and following images are transmitted to the report reading terminal 5 along with the key image, and the preceding and following images are displayed on the report reading terminal 5 along with the key image.

Figure 18:
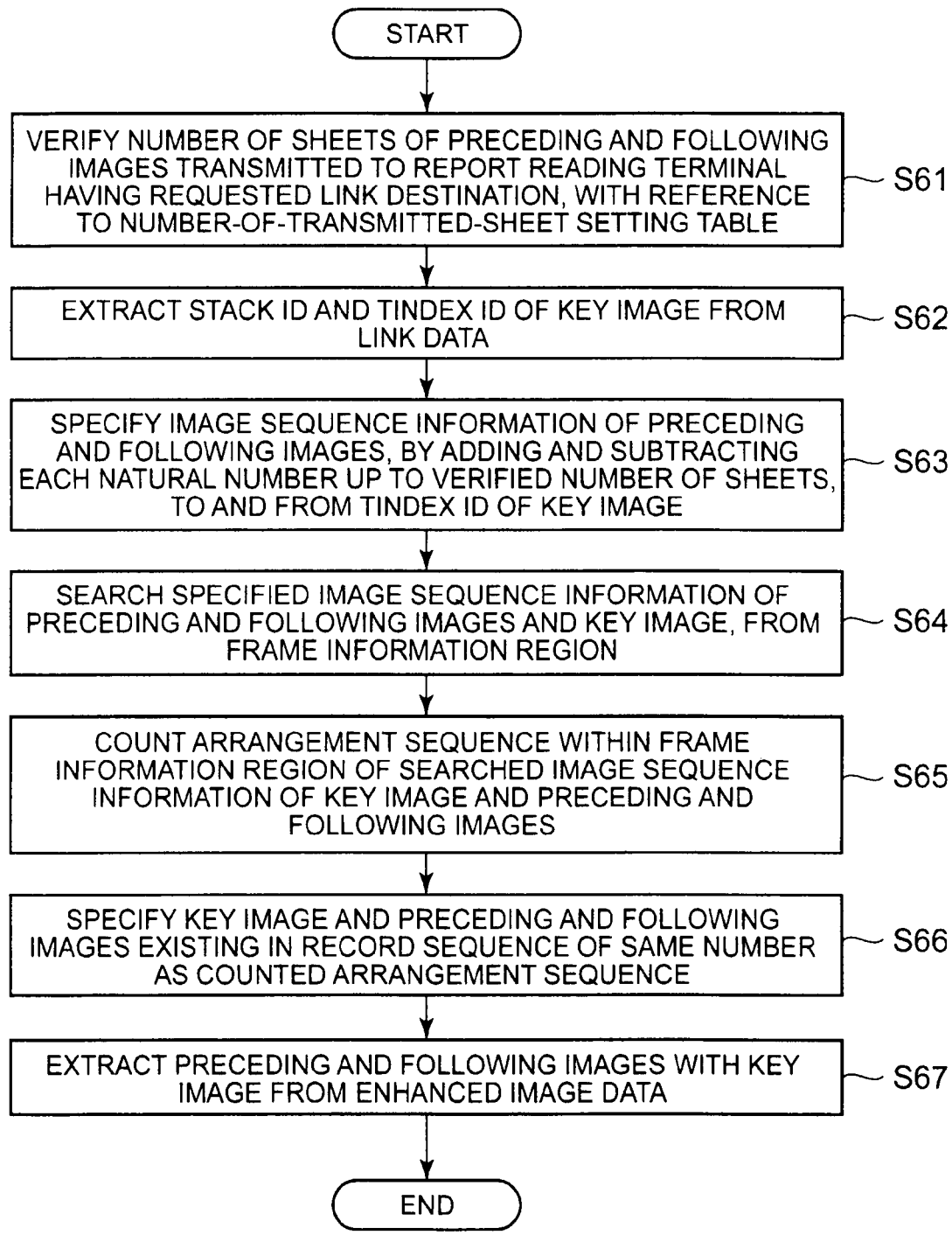
FIG. 18 is a flowchart showing a modification of an operation of transmitting linked medical image data, based on link data containing image sequence information.
Figure 19:
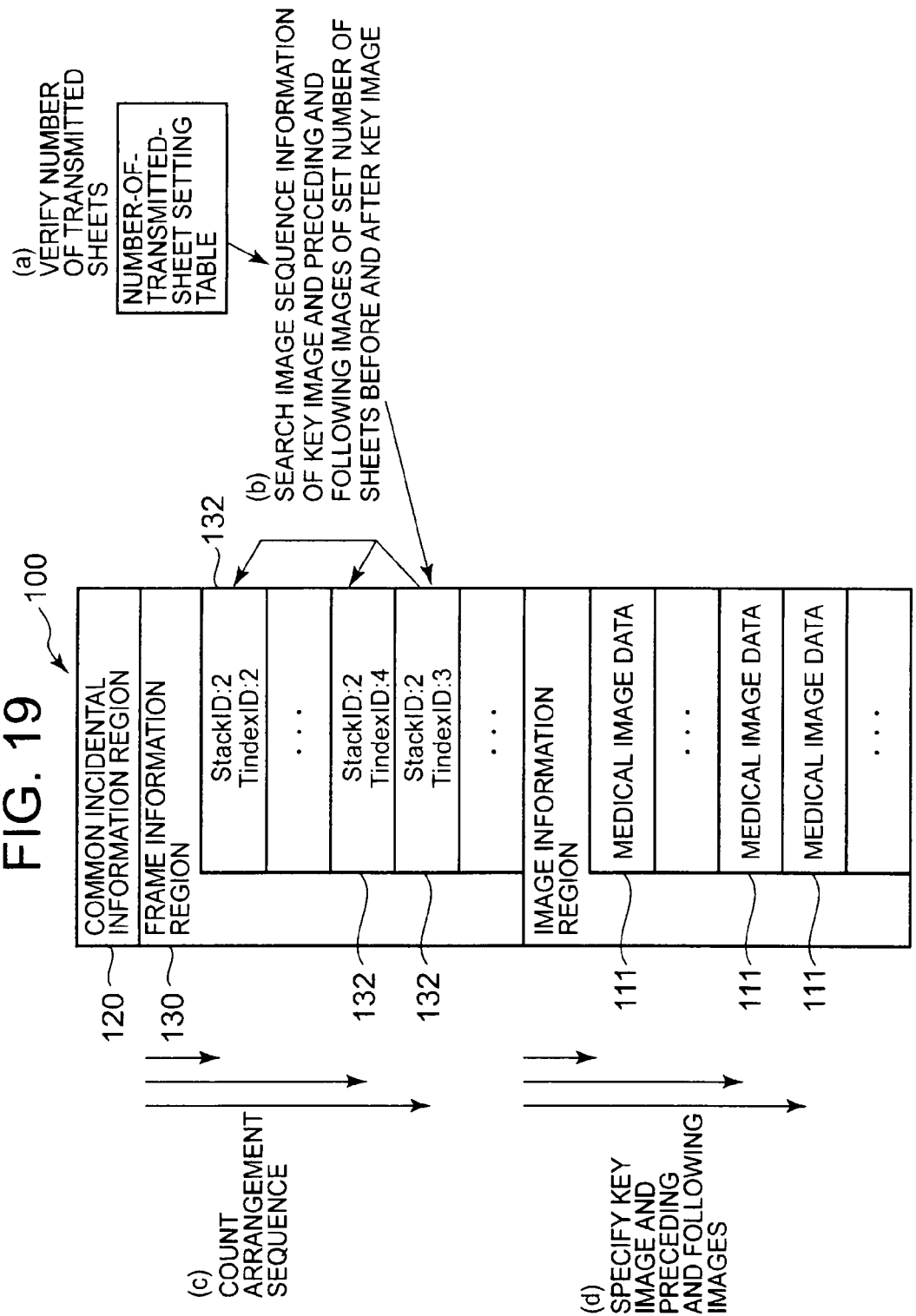
FIG. 19 shows a mode of extracting a plurality of medical images by using link data containing image sequence information.

FIG. 18 is a flowchart showing the modification of the operations for transmitting, to the report reading terminal 5, the medical image data 111 that has been linked by link data containing image sequence information 132. Furthermore, FIG. 19 is a schematic drawing showing a mode of extracting a plurality of medical images using link data containing the image sequence information 132.

First, as shown in FIG. 19A, when the link data is transmitted from the report reading terminal 5, the image specification processor 308 verifies the number of sheets of the preceding and following images to be transmitted to the report reading terminal 5 with reference to the number-of-transmitted-sheet setting table (S61). When verifying the preceding and following number of sheets, the image specification processor 308 extracts the StackID and the TindexID of the key image from the link data (S62), specifies the image sequence information 132 of the preceding and following images by adding and subtracting each natural number to and from the TindexID of the key image, up to the verified number of sheets (S63), and searches from the frame information region 130 as shown in FIG. 19B. When the image sequence information 132 of the preceding and following images are searched, as shown in FIG. 19C, the image specification processor 308 counts the arrangement sequence within the frame information region 130 of the searched image sequence information 132 of the key image and the preceding and following images (S65), and as shown in FIG. 19D, specifies the key image and the preceding and following images existing in the record sequence that is the same number as the counted arrangement sequence (S66), and extracts the same from the enhanced image data 100 (S67). Then, the preceding and following images are transmitted to the report reading terminal 5 along with the key image, and the preceding and following images are displayed on the report reading terminal 5 along with the key image.

In this modification, the number of sheets of the preceding and following images to be transmitted is compiled in a table in association with the report reading terminal 5. However, it is also possible to acquire, from the report reading terminal 5 having requested a link destination, a CPU, a RAM or a configuration such as a broadband and narrowband of the terminal, and calculate the performance of the terminal, thereby determining the number of transmitted sheets based on the result of the calculation.

Furthermore, it is also possible to include the same items as in the file structure management table into the record of the image database 306, and specify the storage destination of the key image or the storage destination of the preceding and following images with reference to the image database 306 without analyzing enhanced image data 100, thereby reading out from the storage destination. In this case, the enhanced image data register 304 analyzes the enhanced image data 100, and stores the memory address number indicating the storage destination in the image storage 305 of the medical image data 111 recorded in the enhanced image data 100, the image sequence information 132 of the medical image data 111, and the offset value, so as to be included in the record of the enhanced image data 100. Then, the image specification processor 308 can extract linked medical image data 111 by reading out, from the image storage 305, the medical image data 111 of the storage destination corresponding to the memory address number paired with the offset value contained in the link data. Furthermore, it is possible to extract the linked medical image data 111, by reading out, from the image storage 305, the medical image data 111 of the storage destination corresponding to the memory address number paired with the image sequence information 132 contained in the link data.

Furthermore, the image specification processor 308 can extract the linked medical image data 111 and the preceding and following medical image data 111 by: reading out the image sequence information 132 paired with the offset value contained in the link data in the image database 306 or using the image sequence information contained in the link data; acquiring the image sequence information 132 of the preceding and following images from the image sequence information 132 and the number-of-transmitted-sheet setting table; and reading out, from the image storage 305, the medical image data 111 of the storage destination corresponding to the memory address number paired with the acquired image sequence information 132.

(Another Modification of Generation of Link data and Image Transmission)

The content of the enhanced image data 100 generated by the medical image diagnosis apparatus 2 may be changed after been registered by the image management server 3. It is required that, even if the content of the enhanced image data 100 is changed, linked medical image data can be specified by using link data having been generated before and can be transmitted to the report reading terminal 5. Hereinafter, generation of link data and specification and transmission of linked medical image data to the report reading terminal 5 on the assumption that the enhanced image data 100 is changed will be described.

Figure 20:
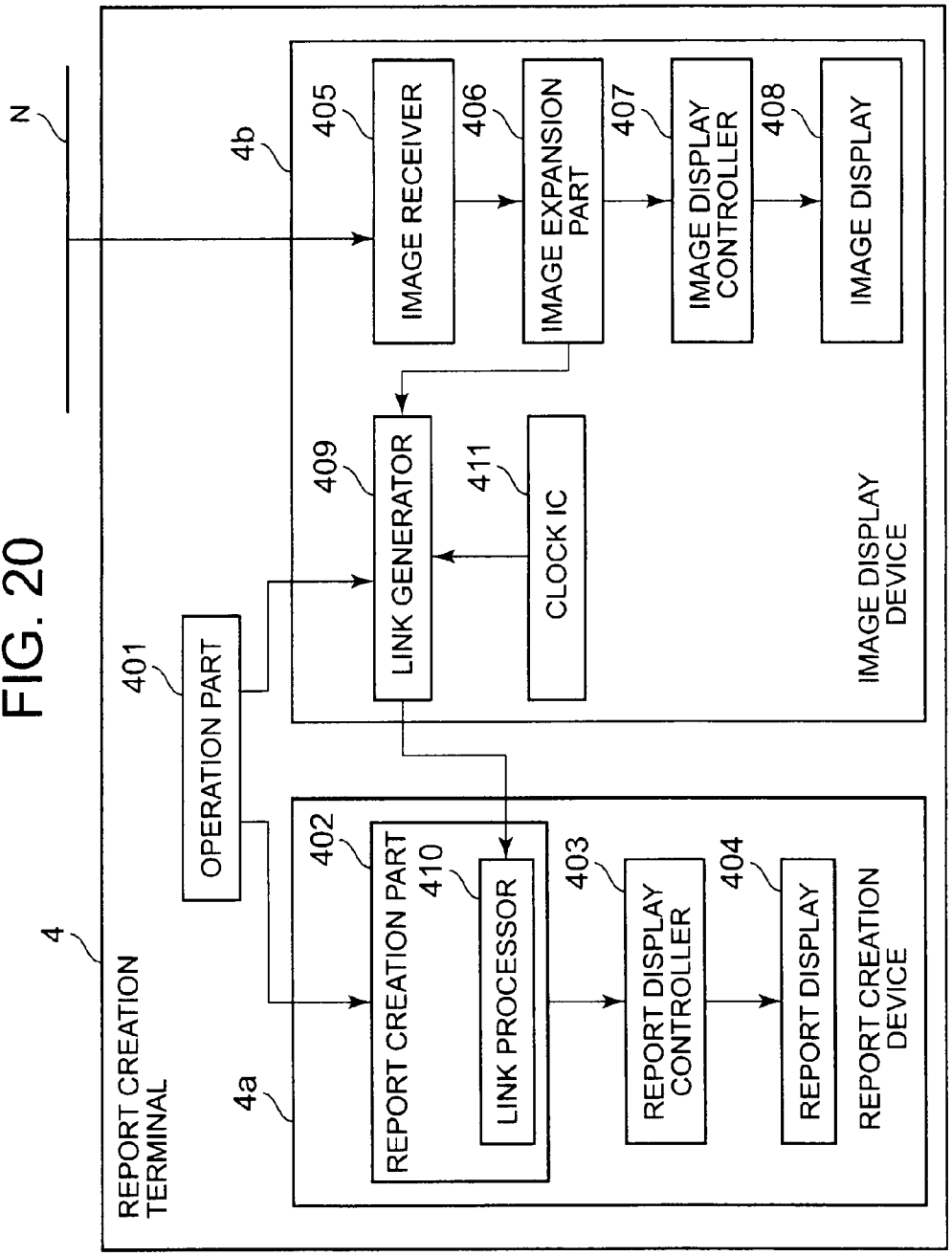
FIG. 20 shows a configuration of a report creation terminal, on the presumption that enhanced image data is changed.

FIG. 20 is a block diagram showing the configuration of the report creation terminal 4 on the assumption that the enhanced image data 100 is changed. The report creation terminal 4 further comprises a clock IC 411. The clock IC 411 measures the current time. The link generator 409 includes generation information into link data by using the clock IC 411.

The generation information included in the link data is information indicating the generation of the enhanced image 100 at the time of generation of the link data. Specifically, the generation information is the date and time at the time of generation of the link data. The link generator 409 acquires date and time information at the time from the clock IC 411 and, at the time of generation of link data, includes the date and time information into the link data as the generation information.

Figure 21:
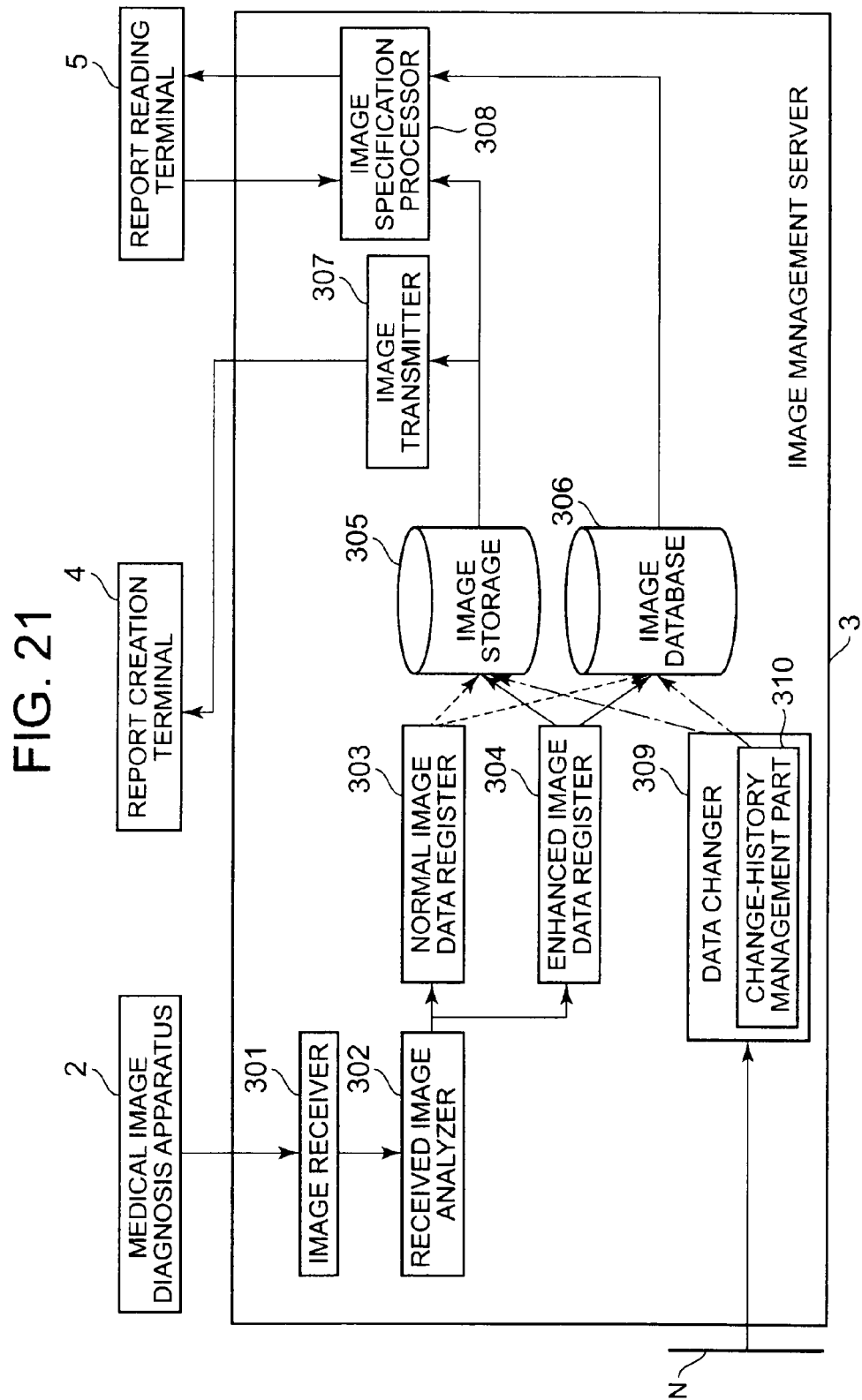
FIG. 21 shows a modification of a configuration of an image management server 3, on the presumption that enhanced image data is changed.

FIG. 21 is a view showing a modification of the configuration of the image management server 3 on the assumption that the enhanced image data 100 is changed.

The image management server 3 further executes change of the data content of normal image data and enhanced image data 100, and management of the change history. The image management server 3 comprises a data changer 309, for the change of the data content of normal image data and enhanced image data 100 and the management of the change history.

The data changer 309 is implemented by execution of an operating system or an image management program by the image management server 3 of a computer.

The data changer 309 mainly comprises a CPU. The data changer 309 changes the content of normal image data and enhanced image data 100. When receiving, from a terminal connected to the network N and handling image data, communication data for changing the content of enhanced image data 100 stored in the image management server 3, the data changer 309 reflects the change content. The communication data contains incidental information of the medical image data 111 described in the frame information region 103 such as the image sequence information 132. The data changer 309 specifies the medical image data 111 subject to deletion from the incidental information contained in the communication data, and reads out the normal image data or enhanced image data 100 to be changed, from the image storage 305, thereby changing. The change of the enhanced image data 100 is, for example, deletion of part of the medical image data 111 recorded in the enhanced image data 100, change of groups of the medical image data 111, and change of the arrangement of images in a group. When receiving communication data for deleting part of the medical image data 111, the data changer 309 deletes, from the enhanced image data 100, the medical image data 111 subject to deletion and the corresponding incidental information described in the frame information region 130. In other words, the data changer 309 deletes the imaging position information 131, image sequence information 132 and so on subject to deletion. Furthermore, the data changer 309 forwards the values of the in-group sequence information 134 within the enhanced image data 100 of the remaining medical image data 111, which are arranged in the same group as the deleted medical image data 111 and after an image of the deleted medical image data 111. The data changer 309 comprises a change-history management part 310 for registering the change content into the image database 306.

The change-history management part 310 registers the change history into the image database 306. The change history includes: information indicating the change content composed of a pair of information before the change and after the change; and generation information indicating the date and time of the change. For example, if the medical image data 111 in a certain sequence number of a certain group is deleted, the change-history management part 310 additionally writes the generation information indicating the date and time of the change into the image database 306, and rewrites the in-group sequence information 134 of each medical image data 111 registered in the image database 306 to information composed of a pair of a sequence number before the change and a sequence number after the change. The change-history management part 310 registers the change history at every change. For example, assuming the medical image data 111 in a certain sequence number of a certain group is deleted twice, the change-history management part 310 additionally writes, into the enhanced image data 100, two new generation information corresponding to the deletions of two times. Furthermore, in response to the second deletion, the change-history management part 310 rewrites the in-group sequence information 134 registered in the image database 306 to information composed of a combination of the sequence number before the change by the first deletion, the sequence number after the change by the first deletion, and the sequence number after the change by the second deletion.

Referring to the change history within the image database 306, the image specification processor 308 specifies the medical image data 111 to which the image specification information contained in the link data corresponds, in the current enhanced image data 100, and extracts the specified medical image data 111.

The generation information may also be information indicating the version as information indicating the generation of the enhanced image data 100. In this case, when storing the enhanced image data 100 into the image management server 3, the enhanced image data register 304 additionally writes, into the enhanced image data 100, the generation information such as "1" or the like, which indicates the first version. Otherwise, when the enhanced image data 100 is generated in the medical image diagnosis apparatus 2, the first generation information is attached. When changing the content of the enhanced image data 100, the data changer 309 changes the generation information within the enhanced image data 100 to a value indicating a new version. The change-history management part 310 additionally writes the generation information indicating the version into the change history. The link generator 409 includes generation information stated in the enhanced image data 100 into link data.

(First Transmission of Linked Image Presuming Change of Enhanced Image Data 100)

Figure 22:
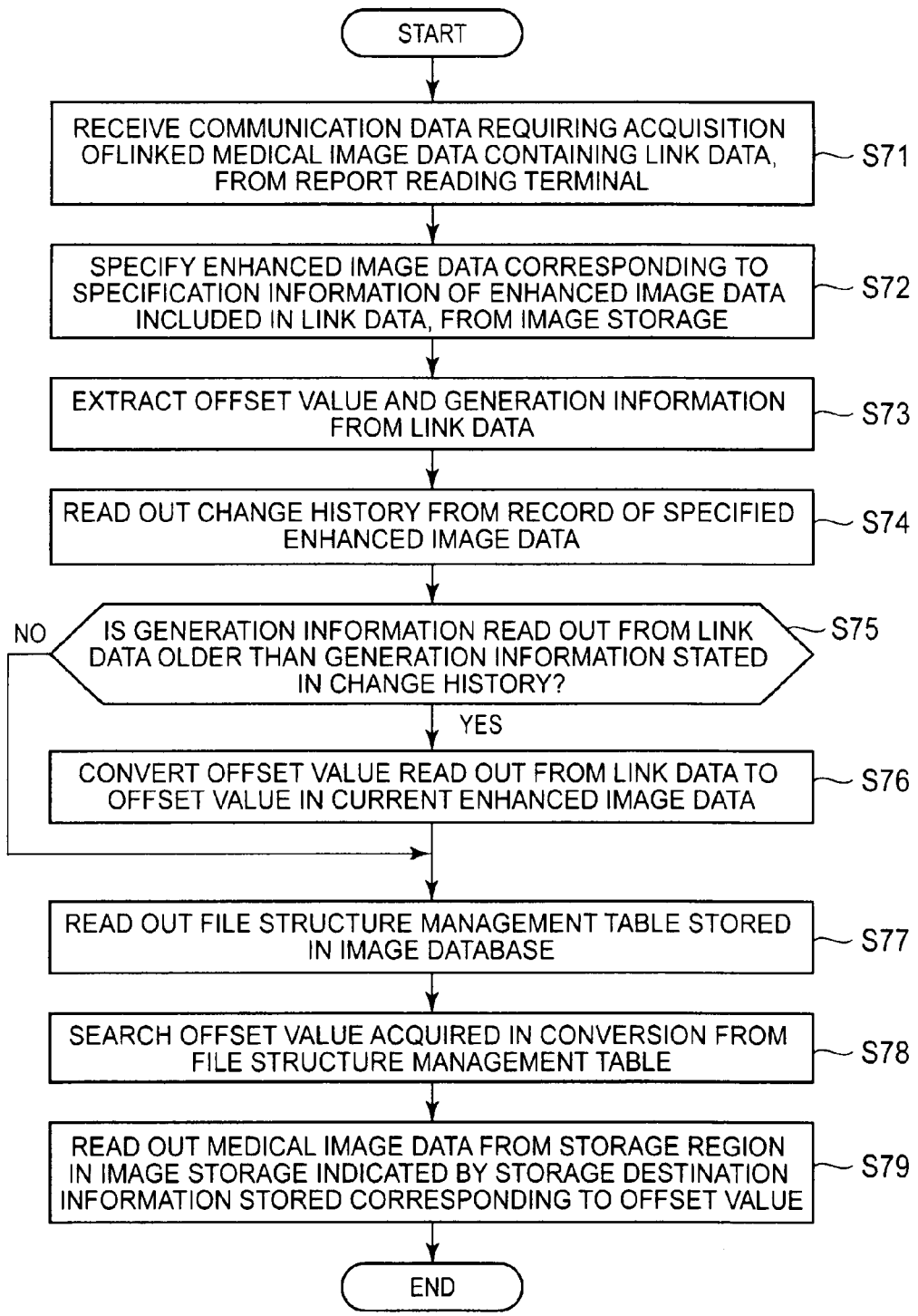
FIG. 22 is a flowchart showing an operation of transmitting linked medical image data, based on link data configured by existing location information, while absorbing a change of enhanced image data.

FIG. 22 is a flowchart showing the operation of absorbing changes of the enhanced image data 100 and, based on link data composed of the existing location information, transmitting linked medical image data 111 to the report reading terminal 5.

First, when the image management server 3 receives communication data including link data and requesting acquisition of linked medical image data 111 from the report reading terminal 5 (S71), the image specification processor 308 extracts specification information of the enhanced image data 100 from the link data, and specifies the enhanced image data 100 from the image storage 305 with reference to the specification information and the image database 306 (S72). Next, the image specification processor 308 extracts an offset value and generation information from the link data (S73), and reads out change history from the record of the specified enhanced image data 100 (S74).

FIG. 23 is an example showing a data configuration of link data created to include existing location information and generation information. For example, if the link data is generated on Jan. 1, 2005, the clock IC 411 records Jan. 1, 2005, which is temporarily stored. Then, when linking for the medical image data 111 starting from the offset value of 900 Kbyte is made in an interpretation report, the link generator 409 generates link data including temporarily stored "20050101" as generation information and "900" as existing location information. The link data, including the generation information and the existing location information is embedded in the interpretation report by the link processor 410.

FIG. 24 is an example showing change history recorded in the image database 306. For example, when the medical image data 111 in data rows of 200 Kbyte to 300 Kbyte of the enhanced image data 100 is deleted by the data changer 309 first on Jan. 1, 2004, in the image database 306, the generation information indicated by "20040101" and the change content indicated by "200-300 deletion" are recorded as change history in the record of the enhanced image data 100 subject to deletion. Furthermore, if the data rows of 200-300 Kbyte is deleted on Jan. 1, 2006, the data rows of 1200-1300 Kbyte is deleted on Jun. 1, 2006 and the data rows of 400-500 Kbyte is deleted on Jan. 1, 2007, the change contents are recorded successively.

The image specification processor 308 reads out the offset value, generation information and change history, and compares the generation information read out from the link data with the generation information stated in the change history (S75). If the generation information read out from the link data is older than the generation information stated in the change history (S75, Yes), the offset value read out from the link data is converted to the offset value in the current enhanced image data 100, with reference to the change content paired with the generation information newer than the generation information read out from the link data within the change history (S76).

For example, the link data in FIG. 23 and the change history in FIG. 24 are used as an example. When the generation information indicated by the "20050101" of the link data and the generation information indicated by the "20040101" of the change history are compared, the generation information of the link data is newer, so that the offset value is not converted. The reason is that the offset value included in the link data is a value on which the change of the enhanced image data 100 on Jan. 1, 2005 has already been reflected. Next, when the generation information indicated by the "20050101" of the link data and the generation information indicated by the "20060101" of the change history are compared, the generation information of the link data is older, so that the offset value included in the link data and the change content are compared. As a result of the comparison, the offset value included in the link data is 900 K, and the deleted data row is 500-600 K, so that the offset value included in the link data comes after the deleted data row. Therefore, the offset value read out from the link data is changed to a value on which the change content is reflected. The reason is that a site indicated by the offset value included in the link data has a forwarded offset value due to the change on Jan. 1, 2006. The image specification processor 308 calculates the size of the deleted data row, and subtracts the calculation result from the offset value read out from the link data. Thus, the offset value read out from the link data is converted to "800 K." Next, when the generation information indicated by the "20050101" of the link data and the generation information indicated by the "20060601" of the change history are compared. The generation information of the link data is older, so that the offset value included in the link data and the change content are compared. As a result of the comparison, the converted value of the offset value included in the link data is 800 K, and the deleted data row is 1200-1300 K, so that the offset value included in the link data is located before the deleted data row. Therefore, the offset value read out from the link data is not converted more. Next, when the generation information indicated by the "20050101" of the link data and the generation information indicated by the "20070101" of the change history are compared, the generation information of the link data is older, so that the offset value included in the link data and the change content are compared. As a result of the comparison, the converted value of the offset value included in the link data is 800 K, and the deleted data row is 400-500 K, so that the offset value included in the link data comes after the deleted data row. Therefore, the offset value read out from the link data is changed to a value on which the change content is reflected. Thus, the offset value read out from the link data is converted to "700 K." The conversion of the read-out offset value is executed for the entire change history. The conversion is performed with respect to the offset value read out from the link data, whereas the offset value included in the link data is not converted.

When the offset value in the current enhanced image data 100 is acquired in this conversion, the file structure management table stored in the image database 306 is read out (S77); the offset value acquired from the conversion is searched (S78); and medical image data 111 is read out from the storage region on the image storage 305 indicated by the storage destination information stored corresponding to the subject offset value (S79). Then, the read-out medical image data 111 is transmitted to the report reading terminal 5 along with the common incidental information region 120 and the frame information region 130 incidental to the enhanced image data 100, whereby the image transmission process ends.

(Second Transmission of Linked Image, Presuming Changes in Enhanced Image Data 100)

Figure 25:
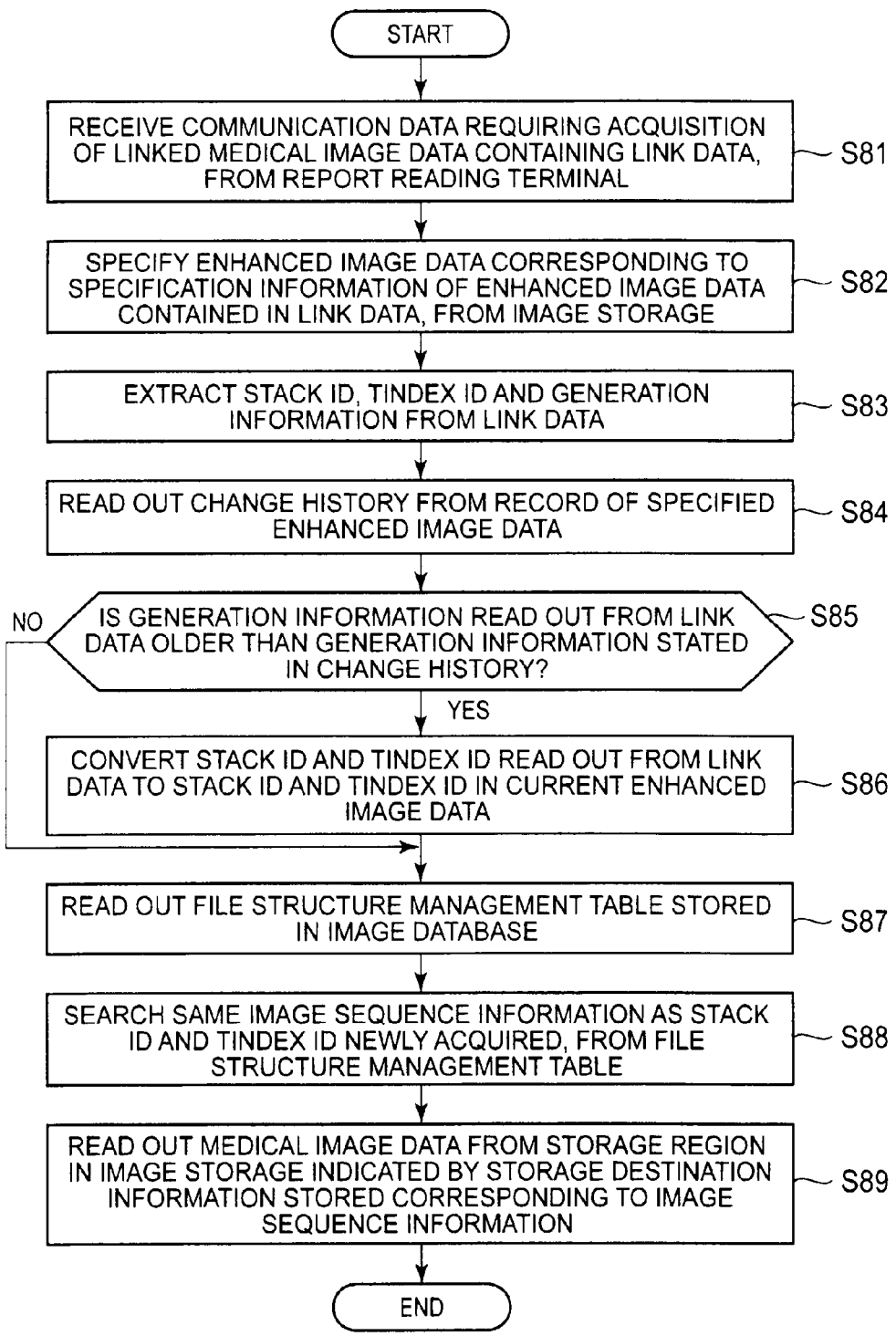
FIG. 25 is a flowchart showing an operation of transmitting linked medical image data, based on link data configured by image sequence information, while absorbing a change of enhanced image data.

FIG. 25 is a flowchart showing the operation of absorbing changes of the enhanced image data 100 and, based on link data composed of the image sequence information 132, transmitting linked medical image data 111 to the report reading terminal 5.

First, when receiving a request for acquiring the linked medical image data 111 containing link data, from the report reading terminal 5 (S81), the image management server 3 extracts specification information of enhanced image data 100 from the link data, and specifies the enhanced image data 100 from the image storage 305 with reference to the specification information and the image database 306 (S82). Next, the image specification processor 308 extracts a Stack ID, a Tindex ID and generation information from the link data (S83), and reads out the change history from the record of the specified enhanced image data 100 (S84).

FIG. 26 is an example showing the data configuration of link data created to include image sequence information 132 and generation information. For example, if the link data is created on Jan. 1, 2006, and linking of StackID:2 and TindexID:4 with respect to the medical image data 111 is made in an interpretation report, the link generator 409 generates link data so as to include "20060101" as generation information and "StackID=2&TindexID=4" as existing location information. The link data containing the generation information and the image sequence information 132 is embedded into the interpretation report by the link processor 410.

FIG. 27 is another example showing change history recorded in the image database 306. For example, in a case where medical image data 111 with StackID:2 and TindexID:3 contained in enhanced image data 100 is deleted by the data changer 309 on Jan. 1, 2007, in the image database 306, the generation information indicated by "20070101," the group information 133 of medical image data that are arranged in the same group as the deleted medical image data 111 and in the image sequence after the deleted medical image data 111, and information before and after the change of the in-group sequence information 134 thereof are recorded as the change history into the record of the enhanced image data 100 subject to deletion. If medical image data 111 with StackID:2 and TindexID:3 is deleted, the fact that the medical image data 111 with StackID:2 and TindexID:4 has been changed to StackID:2 and TindexID:3, and that the medical image data with StackID:2 and TindexID:5 has been changed to StackID:2 and TindexID:4, and so on are recorded.

When reading out the Stack ID and Tindex ID and generation information from the link data and reading out change history from the image database 306, the image specification processor 308 compares the generation information read out from the link data with the generation information stated in the change history (S85). If the generation information read out from the link data is older than the generation information stated in the change history (S85, Yes), the image specification processor 308 converts the StackID and TindexID read out from the link data to a StackID and TindexID in the current enhanced image data 100, with reference to the change content paired with generation information newer than the generation information read out from the link data within the change history (S86).

For example, the link data in FIG. 27 and the change history in FIG. 28 will be used as examples. The generation information indicated by the "20060101" of the link data and the generation information indicated by the "20070101" of the change history are compared. In this case, the generation information of the link data is older, so that it is searched whether the StackID and TindexID contained in the link data exists before the change stated in the change content. As a result of the search, the StackID: 2 and the TindexID: 4 contained in the link data are found in the items of before the change stated in the change content, so that the StackID and the TindexID read out from the link data are changed to the items of after the change stated in the change content. Thus, the StackID and the TindexID read out from the link data are converted to "StackID=2&TindexID=3".

When the StackID and the TindexID in the current enhanced image data 100 are acquired in this conversion, the image specification processor 308 reads out a file structure management table of the enhanced image data 100 stored in the image database 306 (S87), searches the same image sequence information 132 as the StackID and TindexID newly acquired from the file structure management table (S88), and reads out medical image data 111 from a storage region on the image storage 305 indicated by the storage destination information stored corresponding to the image sequence information 132 (S89). Then, the read-out medical image data 111 is transmitted to the report reading terminal 5 along with the common incidental information region 120 and the frame information region 130 incidental to the enhanced image data 100, whereby the image transmission process ends.

Thus, in the medical image management system 1, information that specifies the enhanced image data 100 and existing location information that indicates the location within the enhanced image data 100 of linked medical image data 111 are included into link data, and the image sequence information 132 that indicates the image sequence of the linked medical image data 111 within the enhanced image data 100 is also included, whereby it is possible to set a link to medical image data as one data element within enhanced image data, and extract and read only a linked data row from the enhanced image data.

Consequently, the need for linking the entire enhanced image data is eliminated, so that communication traffic is reduced when reading interpretation reports. Furthermore, effort to search, from the transmitted enhanced image data, medical image data actually cited in the interpretation reports is omitted, so that the medical efficiency increases.

Further, it is possible to configure to, when transmitting the linked medical image data 111, transmit a plurality of medical image data 111 preceding and following the medical image data 111 in the image sequence. As well as the medical image data 111 linked to an interpretation report, the preceding and following medical image data 111 are often regarded as important in a diagnosis or the like. Therefore, conventionally, a person reading an interpretation report acquires the images from the image management server 3 in addition. Alternatively, the person also links these images at the time of creating an interpretation report. This modification makes it possible to read the preceding and following medical image data 111 without requiring such work, so that the clinical efficiency and the interpretation efficiency increase.

Furthermore, it is also possible to attach generation information at the time of reception of the enhanced image data 100 to link data and record the history of change of the enhanced image data 100, thereby comparing the generation information contained in the link data and the change history, and calculating data of the current enhanced image data 100 to which information specifying the medical image data 111 included in the link data corresponds to. Thus, even if the content of the enhanced image data 100 is changed, it is possible to continuously link appropriate medical image data 111 by using the link data within interpretation reports that have been created before the change, which is effective for linking.

What is claimed is:

1. An image management system comprising:
a storage configured to store enhanced image data containing a plurality of medical image data in one file;
a display device configured to display the medical image data contained in the enhanced image data, and display a screen for creating an interpretation report;
a generator configured to generate link data containing image specification information specifying medical image data to link within the enhanced image data, in response to a linking operation by the display device;
a link processor configured to include the link data generated by the generator into data of the interpretation report;
a specification processor configured to specify medical image data indicated by the image specification information in the enhanced image data, from the enhanced image data stored in the storage, based on the link data, in response to an operation of requesting a linked medical image;
an output part configured to output the specified medical image data to a requesting destination of the linked medical image;
wherein the generator includes existing location information representing an existing location within the enhanced image data of medical image data to link, into the link data, as the image specification information; and
the specification processor specifies medical image data existing in a location represented by the existing location information included in the link data, from the enhanced image data stored in the storage.

2. The image management system according to claim 1, wherein:
the generator includes an offset value from a beginning of the enhanced image data, into the link data, as the existing location information; and
the specification processor specifies the medical image data starting from data represented by the offset value included in the link data.

3. The image management system according to claim 1, wherein:
the enhanced image data contains image sequence information of the medical image data;
the generator includes the image sequence information of medical image data to link, into the link data, as the image specification information; and
the specification processor specifies medical image data corresponding to the image sequence information included in the link data, from the enhanced image data stored in the storage.

4. The image management system according to claim 3, wherein:
the enhanced image data contains a plurality of groups of medical image data, and contains a pair of group information to which each of the medical image data belongs and in-group sequence information indicating a sequence of images in the group, as the image sequence information;

the generator includes a pair of the group information and the in-group sequence information into the link data; and the specification processor specifies medical image data corresponding to the group information and in-group sequence information included in the link data, from the enhanced image data stored in the storage.

5. The image management system according to claim 4, wherein:

the group information and the in-group sequence information are a Stack ID and Tindex ID provided in DICOM, respectively, or a Tindex ID and Stack ID provided in DICOM, respectively.

6. The image management system according to claim 1, further comprising:

an enhanced-image-data changer configured to change a record sequence of the medical image data in the enhanced image data, or delete part of the medical image data from the enhanced image data; and a change-history management part configured to store a change history that includes a content of the change by the enhanced-image-data changer and generation information of the enhanced image data accompanying the change, wherein:

the generator further includes the generation information at the time of generation of the link data, into the link data; and the specification processor comprises a change absorption processor configured to specify a location in enhanced image data of a current generation indicated by the existing location information contained in the link data, based on the change history stored in the change-history management part and the generation information included in the link data.

7. The image management system according to claim 3, further comprising:

an enhanced-image-data changer configured to change a record sequence of the medical image data in the enhanced image data, or delete part of the medical image data from the enhanced image data; and a change-history management part configured to store a change history that includes a content of the change by the enhanced-image-data changer and generation information of the enhanced image data accompanying the change, wherein:

the generator further includes the generation information at the time of generation of the link data, into the link data; and the specification processor comprises a change absorption processor configured to specify image sequence information recorded in the enhanced image data of a current generation corresponding to the image sequence information included in the link data, based on the change history stored in the change-history management part and the generation information included in the link data.

8. The image management system according to claim 6, wherein:

the generation information is a date, or data-and-time information.

9. The image management system according to claim 6, wherein:

the generation information is version information.

10. The image management system according to claim 1, wherein:

the enhanced image data contains image sequence information of the medical image data;

the specification processor further specifies, in addition to the medical image data specified in the image specification, a specific number of sheets preceding and following in a sequence of images of the specified medical image data; and the output part also outputs the medical image data specified by the specification processor, to the requesting destination.

11. The image management system according to claim 10, wherein:

the requesting destination is a terminal including a computer; and the specification processor comprises a number-of-transmitted-sheet table storing a pair of terminal identification information identifying the terminal and the specific number of sheets, and further specifies medical image data of the specific number of sheets that forms the pair with the terminal identification information identifying the terminal having requested the linked medical image data, in the number-of-transmitted-sheet table.

12. A medical image management server that has a storage configured to store enhanced image data containing a plurality of medical image data in one file, and transmits, to a terminal displaying an interpretation report, medical image data linked to the interpretation report, the medical image management server comprising:

a receiver configured to receive link data containing image specification information specifying the linked medical image data within the enhanced image data, from the terminal;

a specification processor configured to, when receiving the link data, specify medical image data specified by the image specification information contained in the link data, from the enhanced image data stored in the storage;

an output part configured to output the medical image data specified by the specification processor to the terminal; wherein the enhanced image data contains image sequence information of the medical image data;

the image sequence information of medical image data to link is contained in the link data; and the specification processor specifies medical image data corresponding to the image sequence information contained in the link data, from the enhanced image data stored in the storage.

13. The medical image management server according to claim 12, further comprising:

an enhanced-image-data changer configured to change a record sequence of the medical image data in the enhanced image data, or delete part of the medical image data from the enhanced image data; and a change-history management part configured to store a change history that includes a content of the change by the enhanced-image-data changer and generation information of the enhanced image data accompanying the change, wherein:

the link data further contains the generation information at the time of generation of the link data; and the specification processor comprises a change absorption processor configured to specify a location in the enhanced image data of a current generation indicated by the existing location information contained in the link data, based on the change history stored in the change-history management part and the generation information contained in the link data.

14. The medical image management server according to claim 12, further comprising:

an enhanced-image-data changer configured to change a record sequence of the medical image data in the enhanced image data, or delete part of the medical image data from the enhanced image data; and a change-history management part configured to store a change history that includes a content of the change by the enhanced-image-data changer and generation information of the enhanced image data accompanying the change, wherein:

the link data further contains the generation information at the time of generation of the link data; and the specification processor comprises a change absorption processor configured to specify image sequence information recorded in the enhanced image data of a current generation corresponding to the image sequence information contained in the link data, based on the change history stored in the change-history management part and the generation information contained in the link data.

15. The medical image management server according to claim 12, wherein:

the enhanced image data contains image sequence information of the medical image data;

the specification processor further specifies, in addition to the medical image data specified by the image specification information, a specific number of sheets preceding and following in a sequence of images of the specified medical image data; and the output part also outputs the medical image data having been specified by the specification processor to the terminal.

16. The medical image management server according to claim 12, wherein:

the specification processor comprises a number-of-transmitted-sheet table that stores a pair of terminal identification information identifying a terminal and the specific number of sheets, and further specifies medical image data of the specific number of sheets paired with the terminal identification information identifying the terminal having requested linked medical image data, in the number-of-transmitted-sheet table.

* * * * *